United States Patent [19]

Hesse et al.

[11] Patent Number: 5,786,347
[45] Date of Patent: Jul. 28, 1998

[54] VITAMIN D AMINE AND AMIDE DERIVATIVES

[75] Inventors: Robert Henry Hesse, Winchester; Sundara Katugam Srinivasaetty Setty, Cambridge; Malathi Ramgopal, Andover, all of Mass.

[73] Assignee: Research Institute for Medicine and Chemistry, Inc., Cambridge, Mass.

[21] Appl. No.: 652,597

[22] PCT Filed: Dec. 13, 1994

[86] PCT No.: PCT/GB94/02725

§ 371 Date: Jul. 31, 1996

§ 102(e) Date: Jul. 31, 1996

[87] PCT Pub. No.: WO95/16672

PCT Pub. Date: Jun. 22, 1995

[30] Foreign Application Priority Data

Dec. 13, 1993 [GB] United Kingdom ............... 9325415

[51] Int. Cl.[6] .................... A01N 45/00; C07C 401/00
[52] U.S. Cl. ......................................... 514/167; 552/653
[58] Field of Search ............................ 552/653; 514/167

[56] References Cited

FOREIGN PATENT DOCUMENTS

93/09093  5/1993  WIPO .

*Primary Examiner*—Jose G. Dees
*Assistant Examiner*—Alton Pryor
*Attorney, Agent, or Firm*—Bacon & Thomas

[57] ABSTRACT

The invention relates to vitamin D amine and amide derivatives of general formula

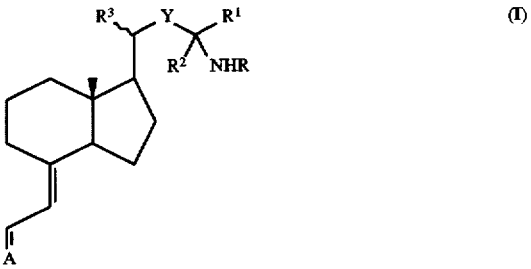

where R represents a hydrogen atom, an aliphatic, cycloaliphatic or araliphatic group, or an acyl group comprising an aliphatic, cycloaliphatic, arylaliphatic or aryl group linked to the nitrogen atom by way of a carbonyl group; $R^1$ and $R^2$ are each selected from lower alkyl and cycloalkyl groups or together with the carbon atom to which they are attached form a lower cycloalkyl group; $R^3$ represents a methyl group having α- or β-configuration; Y represents a lower alkylene, alkenylene or alkynylene group optionally substituted by a hydroxyl, etherified hydroxyl or esterified hydroxyl group; and A= represents a cyclohexylidene moiety characteristic of the A-ring of a 1 α-hydroxylated vitamin D or analogue thereof. Active compounds of the invention exhibit cell modulating activity and in certain cases may also have an effect on calcium metabolism. The compounds of the invention may be prepared by isomerizing a 5,6-trans isomer of formula (I) to a corresponding 5,6-cis isomer; by hydroxylating a 1-unsubstituted-5,6-trans analogue of a compound of formula (I) to prepare a 5,6-trans isomer of formula (I); by reacting a compound containing a precursor for the desired 17-position side chain in one or more stages and with one or more reactants serving to form the desired side chain; or by reacting a compound of formula (I) to modify the substitution pattern about the A= group.

15 Claims, No Drawings

VITAMIN D AMINE AND AMIDE DERIVATIVES

This invention relates to novel vitamin D analogues, more particularly to 1α-hydroxy vitamin $D_3$ analogues having a modified side chain at the 17-position.

Vitamin $D_3$, which has the formula

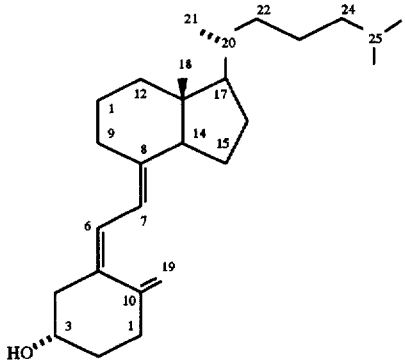

is well known to play a vital role in the metabolism of calcium, by promoting intestinal absorption of calcium and phosphorus, maintaining adequate serum levels of calcium and phosphorus and stimulating mobilisation of calcium from the bone fluid compartment in the presence of parathyroid hormone.

It was learned more than 20 years ago that the D vitamins undergo hydroxylation in vivo, hydroxylation at the 25-position occurring in the liver and hydroxylation at the 1α-position occurring in the kidney, the resulting 1α,25-dihydroxy metabolite being the biologically active material. This discovery led to the synthesis of many analogues of vitamin D, evaluation of which indicated that hydroxyl groups at the 1α-position a and at either the 24R- or the 25-position were essential for a compound or metabolite thereof to exhibit a substantial effect on calcium metabolism. While, as indicated above, such hydroxyl groups will normally ultimately be introduced in vivo, hydroxylation at the 24R- or 25-position occurring rather more readily than at the 1α-position, the use of vitamin D analogues already so hydroxylated has proved of substantial advantage by virtue of their enhanced levels of activity and their rapidity of action and subsequent elimination from the body. It will be appreciated that 1α-hydroxylated vitamin D derivatives are of especial benefit to patients suffering from renal failure.

Examples of hydroxylated vitamin D analogues in current use include the natural metabolite 1α,25-dihydroxy vitamin $D_3$ and 1α-hydroxy vitamin $D_3$ (which is readily 25-hydroxylated in vivo). Other reportedly promising compounds include 1 α,24R-dihydroxy vitamin $D_3$, $D_2$ analogues of the above compounds and 1α,25-dihydroxy analogues carrying fluorine atoms at the 24-, 26- and/or 27-positions (see De Luca and Schnoes, Ann. Rev. Biochem. (1983), 52, pp 411–439 and De Luca et al., Top. Curr. Chem. (1979), 83, pp 1–65).

More recently it has been learned that the natural metabolite 1α,25-dihydroxy vitamin $D_3$ has additional effects on cellular metabolism. These cell modulating effects include stimulation of cell maturation and differentiation (Tanaka et al., Biochem. J. (1982), 204, pp 713–719; Amento et al., J. Clin. Invest, (1984),73, pp 731–739; Colston et al., Endocrinology (1981), 108, pp 1083–1086; Abe et al., Proc. Nat, Acad. Sci. (1981), 78, pp 4990–4994) and immunosuppressive effects (e.g. inhibition of interleukin II production) (Rigby, Immunology Today (1988), 9, pp 54–58).

Still more recently, an immunopotentiating effect of 1α,25-dihydroxy vitamin $D_3$ has been observed, the compound having been found to stimulate the production of bactericidal oxygen metabolites and the chemotactic response of leukocytes (see, for example, Cohen et al., J. Immunol. (1986), 136, pp 1049–1053). It is well known that leukocytes play a major role in the body's defence against various infections (see, for example, Roitt, Brostoff and Male, "Immunology" 2nd Ed. (1989), C. V. Mosby, St. Louis, sec 16.10–16.13 and 17.4–17.5), e.g. by adhering to and engulfing invading organisms (chemotactic response) and/or by producing superoxides and/or other toxic oxygen metabolites. It is known that this response may also be stimulated by mitogens such as the co-carcinogenic phorbal esters and γ-interferon, which are structurally quite different from vitamin D analogues.

By virtue of these effects on cellular metabolism, 1α,25-dihydroxy vitamin $D_3$ in principle has therapeutic potential in such diverse areas as treatment of psoriasis, inflammatory and autoimmune diseases, neoplasias and hyperplasias, as an adjunct in the chemotherapy of infections (inter alia bacterial, viral and fungal), and in other therapeutic modalities in which mononuclear phagocytes are involved. 1α,25-dihydroxy vitamin $D_3$ and 1α-hydroxy vitamin $D_3$ have also been proposed for use in the treatment of hypertension (Lind et al., Acta Med. Scand. (1987), 222, pp 423–427) and diabetes mellitus (Inomata et al., Bone Mineral (1986), 1, pp 187–192), and it has been suggested that 1α,25-dihydroxy vitamin $D_3$ may promote hair growth (Lancet, 4 Mar. 1989, p 478) and may be useful in the treatment of acne (Malloy et al., Tricontinental Meeting for Investigative Dermatology, Washington, 1989).

The potent effects of 1α,25-dihydroxy vitamin $D_3$ and 1α-hydroxy vitamin $D_3$ on calcium metabolism will, however, normally preclude such uses, since dosages at a level sufficient to elicit a desired cell modulating, immunosuppressive or immunopotentiating effect tend to lead to unacceptable hypercalcaemia. This has led to attempts to synthesize new analogues having reduced effects on calcium metabolism but which still exhibit the desired effects on cellular metabolism.

There have been reports of new analogues which exhibit, to at least a moderate degree, this desired separation of activity. Thus the compound MC-903 (calcipotriol), which is a 22,23-unsaturated 1α,24R-dihydroxy vitamin $D_3$ analogue carrying a cyclopropyl group at the 24-position instead of the usual $C_{25-C27}$ configuration of the cholestane side chain, and which is now used for the treatment of psoriasis, is reported to exhibit an effect on cell maturation comparable in magnitude to 1α,25-dihydroxy vitamin $D_3$, while exhibiting a smaller hypercalcaemic effect (Calverley, Tetrahedron (1987), 43, pp 4609–4619; and Holick, Arch, Dermatol. (1989), 125, pp 1692–1696). Similar claims have been made for analogues of 1α,25-dihydroxy vitamin $D_3$, e.g. the 22-oxa (Abe et al., Endocrinology (1989), 124, pp 2645–2647), the 24- and the 26- homo (Ostrem et al., J. Biol, Chem. (1987), 262, pp 14164–14171), the 16-dehydro-23,24-ethynyl (Zhou et al., Blood (1989), 74, pp 82–93) and the 19-nor-1-dihydro (Perlman et al., Tetrahedron Lett. (1990), pp 1823–1824).

Other analogues of 1α,25-dihydroxy vitamin $D_3$ which have been studied with the aim of achieving enhanced separation of differentiation-inducing activity and hypercalcaemic effect include 23-oxa, 23-thia and 23-aza derivatives (Kubodera et al., Chem. Pharm. Bull. (1991), 39, pp 3221–3224), 22-oxa analogues bearing side chains of different sizes (Kubodera et al., Chem. Pharm. Bull. (1992), 40, pp 1494–1499), and 20-epi analogues (Binderup et al., Biochemical Pharmacology (1991), 42, pp 1569–1575).

It does not appear possible to deduce from these disclosures either which compounds will exhibit cell modulating activity(or the level of any such activity) or to determine factors which lead to a separation of activities as regards cell modulation and calcium metabolism. Thus, for example, it has been observed that there are no strict relationships between differentiation-inducing activity and side chain length or hydrophilicity.

The majority of results suggest that the presence of a hydroxyl group towards the end of a cholestane-type side chain or homologue thereof is necessary for compounds to show significant cell modulating activity. However, the findings of Ostrem et al. (op. cit.) indicate that analogues having only a short, unsubstituted 17-position side chain (e.g. isopropyl or sec-butyl, as in homo- or bis-homo-pregnanes) exhibit quite substantial-differentiation-inducing activity and are more potent than corresponding short side chain compounds bearing a side chain hydroxyl group.

A number of the proposed analogues appear to show cell modulating activity at a similar level to that of $1\alpha,25$-dihydroxy vitamin $D_3$, but also appear still to show appreciable effects on calcium metabolism, such activity being attenuated by at most two orders of magnitude relative to that of $1\alpha,25$-dihydroxy vitamin $D_3$. Moreover, it now appears in the case of many, if not all, of the new analogues described above as exhibiting separation of calcium and cellular metabolic effects, including MC-903, that the attenuated calcium effect may be due merely to more rapid metabolism of the vitamin reducing the amount of the circulating drug (see e.g. Bouillon et al., *J. Bone Miner. Res.* (1991), 6, p 1051 and Dusso et al., *Endocrinology* (1991), 128, p 1687). This may similarly reduce the cell modulating effect in vivo so that one may require larger systemic dosages than are suggested by in vitro test results.

Use of such analogues may therefore give rise to cumulative toxicity problems if the compounds are used in long term therapy, particularly where systemic application is required, e.g. for treatment of inflammatory and autoimmune diseases, neoplasias and hyperplasias, or in oral therapy for treatment of psoriasis, and there is thus a continuing need in such areas of therapy for vitamin D-like compounds which exhibit potent cell modulating activity coupled with a reduced effect on calcium metabolism.

There may also be circumstances in which a particular balance of cell modulating and calcium metabolising properties is desired. This may be the case in, for example, the treatment of osteoporosis. The present invention is based on the finding that $1\alpha$-hydroxy vitamin D derivatives in which the 17-position side chain carries certain amine or amide functions may exhibit useful biological activity; this is most surprising in that the invention includes is compounds which lack a side chain hydroxyl group; such a group has hitherto normally been thought desirable in order to promote calcaemic and/or cell modulating activity. Furthermore, as noted by Kubodera et al. (op. cit., 1991), introduction of a nitrogen atom into the 17-position side chain of $1\alpha,25$-dihydroxy vitamin $D_3$ to replace a methylene group thereof appears to be deactivating as regards differentiation-inducing activity. One might therefore expect replacement of the activity-promoting side chain hydroxyl group of a vitamin D analogue by an amine or amide function to be even more deactivating, especially since amine groups are very significantly more basic than oxygen functions such as hydroxyl groups, and are protonated at physiological pH.

Additionally, as is described in greater detail hereinafter, it has been found that by appropriate selection of e.g. the size of the carbon chain of the 17-position side chain of the compounds according to the invention it is possible to influence their activity by enhancing either cell modulating properties or activity as regards calcium metabolism and bone calcium mobilisation, thereby making possible the preparation of compounds with particular activity profiles suited to particular therapeutic applications.

Thus according to one aspect of the present invention there are provided compounds of formula (I)

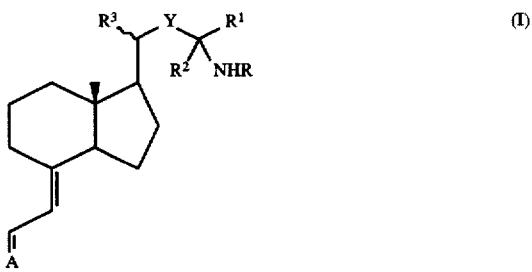

(where R represents a hydrogen atom, an aliphatic, cycloaliphatic, araliphatic or aryl organic group, or an acyl group comprising such an organic group linked to the nitrogen atom by way of a carbonyl group; $R^1$ and $R^2$, which may be the same or different, each represent a lower alkyl or cycloalkyl group or together with the carbon atom to which they are attached form a lower cycloalkyl group; $R^3$ represents a methyl group having $\alpha$-or $\beta$-configuration; Y represents a lower alkylene, alkenylene or alkynylene group optionally substituted by a hydroxyl, etherified hydroxyl or esterified hydroxyl group; and A= represents a cyclohexylidene moiety characteristic of the A-ring of a $1\alpha$-hydroxylated vitamin D or analogue thereof.

Where either of $R^1$ and $R^2$ represent lower alkyl groups these may, for example, be $C_{1-6}$ alkyl groups such as methyl, ethyl, propyl and butyl groups. Lower cycloalkyl groups $R^1$ and $R^2$ may, for example, contain 3–8 carbon atoms, e.g. as in cyclopropyl, cyclopentyl and cyclohexyl groups.

Where R represents an aliphatic or cycloaliphatic group this may, for example, be a lower alkyl or lower cycloalkyl group, e.g. as described for $R^1$ and $R^2$. Araliphatic groups R may, for example, include $C_{6-12}$ carbocyclic aryl $C_{1-4}$ alkyl groups such as benzyl or phenethyl; aryl groups may, for example, include $C_{6-12}$ carbocyclic aryl groups such as phenyl or naphthyl. Where R represents an acyl group this may, for example, be a lower (e.g. $C_{1-6}$) alkanoyl group such as formyl, acetyl or propionyl; a $C_{6-12}$ carbocyclic aryl $C_{2-5}$ alkanoyl group such as phenylacetyl; or a $C_{7-13}$ carbocyclic aroyl group such as benzoyl. The group R may optionally carry one or more substituents, for example selected from halo (e.g. chloro or bromo), lower (e.g. $C_{1-4}$) alkyl such as methyl, lower alkoxy (e.g. methoxy), lower alkanoyl (e.g. acetyl), lower alkylamino (e.g. methylamino), di(lower alkyl)amino (e.g. dimethylamino), nitro, carbamoyl and lower alkanoylamino (e.g. acetamido).

Lower alkylene, alkenylene or alkynylene groups represented by Y may, for example, contain up to 7 carbon atoms and up to 3 multiple bonds. Y may advantageously be a straight chained group, e.g. containing 3–6 carbon atoms, for example as in trimethylene, tetramethylene, pentamethylene, hexamethylene, buta-1,3-dienylene, propynylene, but-1-ynylene or but-2-ynylene.

Where Y is substituted by a hydroxyl, etherified hydroxyl or esterified hydroxyl group, this substituent may advantageously be positioned $\alpha$-, $\beta$- or $\gamma$- to the group —$C(R^1)(R^2)$.NHR or $\alpha$- to any triple bond present in the group Y. Etherified hydroxyl groups which may be present inclkude lower (e.g. $C_{1-6}$) alkyl groups optionally interrupted by one or more oxygen atoms (e.g. methyl, methoxymethyl or methoxyethoxymethyl), and cyclic groups such as tetrahydropyranyl. Esterified hydroxyl groups which may be present include lower (e.g. $C_{1-6}$) alkanoyl such as acetyl, propionyl, isobutyryl or pivaloyl; lower alkenoyl (e.g. allylcarbonyl); aroyl (e.g. p-nitrobenzoyl); lower alkoxycarbonyl (e.g. t-butoxycarbonyl); lower haloalkoxycarbonyl (e.g. 2,2,2-trichloroethoxycarbonyl or 1,1,1-trichloro-2-methyl-2-propoxycarbonyl); aralkyloxycarbonyl (e.g. benzyloxycarbonyl or p-nitrobenzyloxycarbonyl); and lower alkenyloxycarbonyl (e.g. allyloxycarbonyl). It will be appreciated that it may be advantageous to select etherifying or esterifying groups which are metabolically labile in vivo.

Where $R^3$ in formula (I) is a methyl group in the α-configuration the compounds have the 20R configuration characteristic of natural vitamin D derivatives; where $R^1$ is in the β-configuration the compounds have the 20S configuration of epi-vitamin D derivatives. It will be appreciated that the invention also embraces mixtures of the two isomers.

The cyclohexylidene ring represented by A= will normally carry hydroxyl groups or protected derivatives thereof at the 1α- and 3β-positions, and may carry further substituents, e.g. which tend to enhance calcaemic or antiproliferative activity and/or stimulate differentiation. A= may thus, for example, be represented by the formula (A-1)

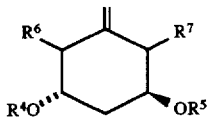

where $R^4$ and $R^5$, which may be the same or different, each represent a hydrogen atom or an O-protecting group, and $R^6$ and $R^7$, which may the same or different, are selected from hydrogen atoms and appropriate mono- or di-valent substituting groups.

Where $R^4$ and $R^5$ represent O-protecting groups these may, for example, be cleavable O-protecting groups such as are commonly known in the art. Suitable groups include etherifying groups such as silyl groups (e.g. tri (lower alkyl) silyl groups such as trimethylsilyl, triethylsilyl, triisopropylsilyl or t-butyldimethylsilyl; tri (aryl) silyl groups such as triphenylsilyl; and mixed alkyl-arylsilyl groups); lower (e.g. $C_{1-6}$) alkyl groups optionally interrupted by an oxygen atom, such as methyl, methoxymethyl or methoxyethoxymethyl; and cyclic groups such as tetrahydropyranyl. Esterifying O-protecting groups include lower (e.g. $C_{1-6}$) alkanoyl such as acetyl, propionyl, isobutyryl or pivaloyl; aroyl (e.g. containing 7–15 carbon atoms) such as benzoyl or 4-phenylazobenzoyl; lower alkane sulphonyl such as (optionally halogenated) methane sulphonyl; and arene sulphonyl such as p-toluene sulphonyl.

O-protected derivatives are useful as intermediates in the preparation of active 1α,3β-diols of formula (I) where $R^4$ and $R^5$ represent hydrogen atoms. Additionally, where the O-protecting groups are metabolically labile in vivo, such ethers and esters of formula (I) may be useful directly in therapy.

At least one of $R^6$ and $R^7$ is advantageously a hydrogen atom. Substituents which may be present as the other of $R^6$ and $R^7$ include, for example, methylene, methyl and ethylene (so as to form a spiro-linked cyclopropyl group with the attached carbon atom).

Representative A= groups falling within the above formula A-1) include the following:

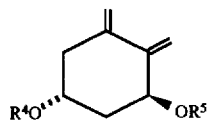

(A-2)

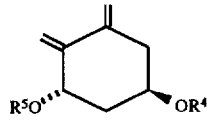

(A-3)

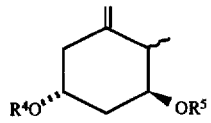

(A-4)

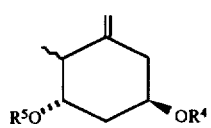

(A-5)

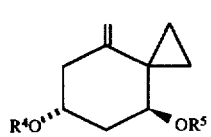

(A-6)

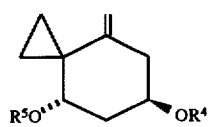

(A-7)

and

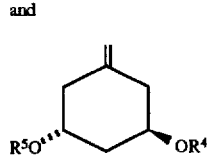

(A-8)

It will be appreciated that compounds containing groups (A-2) and (A-3) are respectively 5,6-cis (i.e. 5 Z) and 5,6-trans (i.e. 5 E) isomers of vitamin D analogues. Compounds containing groups (A-4) and (A-5) are similarly 5,6-cis and 5,6-trans isomers respectively of 10,19-dihydro vitamin D analogues, and compounds containing group (A-8) are 19-nor vitamin D analogues.

5,6-Trans isomers according to the invention are principally of interest as intermediates in the preparation of corresponding 5,6-cis isomers, e.g. as described in greater detail hereinafter. However, 5,6-trans isomers in which $R^4$ and $R^5$ are hydrogen atoms or metabolically labile groups will often exhibit biological activity, e.g. at about one order of magnitude less than corresponding 5,6-cis isomers, and may thus be useful in therapy.

Active compounds of formula (I) in which Y is, for example, a group containing up to 3 carbon atoms such as trimethylene and $R^1$ and $R^2$ are, for example, lower alkyl groups such as methyl or ethyl may exhibit similar activity to known 1α-hydroxy vitamin D derivatives such as 1α,25-dihydroxy vitamin $D_3$. Thus, for example, such compounds may exhibit a significant effect on calcium metabolism, e.g. by stimulating intestinal calcium transport, bone calcium mobilisation and bone formation. These compounds may therefore have applications in, for example, treatment and/or prevention of disorders such as rickets and osteomalacia, osterporosis, hypoparathyroidism, hypophosphateamia, hypocalcaemia and/or associated bone disease, hypocalcaemic tetany, renal failure and disorders such as renal osteodystrophy, biliary cirrhosis and steatorrhea, and secondary hypocalcaemia and/or bone disease arising from disfunction of the liver, kidneys or gastrointestinal tract or resulting from treatment with dilantin, barbiturates such as phenylbarbitone and related drugs; they may be particularly useful in treating disorders which are refractory to natural compounds such as vitamin $D_3$.

The presence of an amino group in compounds of formula (I) in which R represents hydrogen or a lower alkyl group may enhance the bioavailability of the compounds relative to vitamin D derivatives containing a side chain hydroxyl group, for example by limiting sequestration in liposomes, and may also permit the compounds readily to be formulated as aqueous compositions, a highly advantageous property compared to conventional oil-soluble vitamin D derivatives.

The above-described compounds of formula (I) also exhibit cell modulating activity, e.g. as evidenced by eliciting cell differentiation and maturation, inhibiting proliferation and/or by activating monocytes (e.g. as estimated by the method of Styrt et al., Blood (1986), 67, pp 334–342), but their calcaemic effects may be too pronounced to permit e.g. mid- or long-term use in respect of their cellular metabolic effects. The higher homologues of these compounds, however, e.g. compounds (I) in which Y contains 4–7 carbon atoms and/or $R^1$ and/or $R^2$ each contain 2 or more carbon atoms, may tend to exhibit a reduced effect on calcium metabolism, e.g. as evidenced by low effects on serum calcium and phosphorus levels in rats, and may accordingly exhibit an advantageous therapeutic ratio of cell modulating to calcaemic activity.

The cell modulating activity of such active compounds according to the invention, combined with a substantial lack of calcaemic effect, render them of interest (both alone and as adjuncts) in the management of neoplastic disease, particularly myelogenous leukemias, and suggest their use as agents to promote wound healing. They may also be used either alone or as adjuncts in the chemotherapy of infection and in all other therapeutic modalities in which mononuclear phagocytes are involved, for example in treatment of bone disease (e.g. osteoporosis, osteopenia and osteodystrophy as in rickets or renal osteodystrophy), autoimmune diseases, host-graft reaction, transplant rejection, inflammatory diseases (including modulation of immunoinflammatory reactions), neoplasias and hyperplasias, myopathy, enteropathy and spondylitic heart disease. Such active compounds according to the invention may also be useful in suppression of parathyroid hormone (e.g. as in serum calcium homeostasis), in treatment of dermatological diseases (for example including acne, alopecia, eczema, pruritus, psoriasis and skin aging, including photoaging), hypertension, rheumatoid arthritis, psoriatic arthritis, secondary hyperparathyrodism, asthma, cognitive impairment and senile dementia (including Alzheimer's disease), in fertility control in both human and animal subjects, and in management of disorders involving blood clotting, e.g. by dissolution of existing clots and/or prevention of clotting. The invention embraces use of these compounds in the therapy or prophylaxis of such conditions and in the manufacture of medicaments for such treatment or prophylaxis.

We believe that the active 20R isomers of such compounds of formula (I) may be preferred for treatment of infections, e.g. in combination therapy, whereas the active 20S epi-isomers may be preferred for applications involving an immunosuppressive effect, e.g. in treatment of autoimmune and inflammatory diseases, rheumatoid arthritis, asthma etc. This view is supported by, for example, the work of Binderup et al. concerning 20-epi-vitamin $D_3$ analogues reported in Biochemical Pharmacology (1991), 42(8), pp 1569–1575.

It will be appreciated that it may be preferred to select lower homologues according to formula (I) for treatment of e.g. defects of calcium metabolism and to select higher homologues specifically for their cell modulating activity, e.g. in treatment of hyperplasias such as psoriasis. However, both types of activity may be useful in, for example, treatment of bone disease, and particular homologues may therefore be chosen by selection of appropriate meanings for Y, $R^1$ and $R^2$ in order to give a desired balance of activities for such purposes.

It has been reported (Neef et al., 9th Workshop on Vitamin D (1994) that in the case of vitamin D compounds having conventional terminally hydroxylated 17-position side chains (including side chains containing a heteroatom at the 23-position), analogues having 20,20-dimethyl, 20-methylene or 20-spirocyclopropyl groups may exhibit useful biological activity, typically resembling that of the corresponding 20R methyl-substituted isomer rather than the corresponding 20S epi-isomer. The present invention embraces analogues of the above-defined compounds of formula (I) wherein $R^3$ is selected from dimethyl, methylene and spirocyclopropyl groups.

Active compounds according to the invention may be formulated for administration by any convenient route, e.g. orally (including sublingually), parenterally, rectally or by inhalation; pharmaceutical compositions so formulated comprise a feature of the invention.

Orally administrable compositions may, if desired, contain one or more physiologically compatible carriers and/or excipients and may be solid or liquid. The compositions may take any convenient form including, for example, tablets, coated tablets, capsules, lozenges, aqueous or oily suspensions, solutions, emulsions, syrups, elixirs and dry products suitable for reconstitution with water or another suitable liquid vehicle before use. The compositions may advantageously be prepared in dosage unit form. Tablets and capsules according to the invention may, if desired, contain conventional ingredients such as binding agents, for example syrup, acacia, gelatin, sorbitol, tragacanth or polyvinyl-pyrollidone; fillers, for example lactose, sugar, maize-starch, calcium phosphate, sorbitol or glycine; lubricants, for example magnesium stearate, talc, polyethylene glycol or silica; disintegrants, for example potato starch; or acceptable wetting agents such as sodium lauryl sulphate. Tablets may be coated according to methods well known in the art.

Liquid compositions may contain conventional additives such as suspending agents, for example sorbitol syrup, methyl cellulose, glucose/sugar syrup, gelatin, hydroxymethylcellulose, carboxymethylcellulose, aluminium stearate gel or hydrogenated edible fats; emulsifying agents, for example lecithin, sorbitan monooleate or acacia; non-aqueous vehicles, which may include edible oils, for example vegetable oils such as arachis oil, almond oil, fractionated coconut oil, fish-liver oils, oily esters such as polysorbate 80, propylene glycol, or ethyl alcohol; and preservatives, for example methyl or propyl p-hydroxybenzoates or sorbic acid. Liquid compositions may conveniently be encapsulated in, for example, gelatin to give a product in dosage unit form.

Compositions for parenteral administration may be formulated using an injectable liquid carrier such as sterile pyrogen-free water, sterile peroxide-free ethyl oleate, dehydrated alcohol or propylene glycol or a dehydrated alcohol/propylene glycol mixture, and may be injected intravenously, intraperitoneally or intramuscularly.

Compositions for rectal administration may be formulated using a conventional suppository base such as cocoa butter or another glyceride.

Compositions for topical administration include ointments, creams, gels, lotions, shampoos, paints, powders (including spray powders), pessaries, tampons, sprays, dips, aerosols, pour-ons and drops. The active ingredient may, for example, be formulated in a hydrophilic or hydrophobic base as appropriate.

Compositions for administration by inhalation are conveniently formulated for self-propelled delivery, e.g. in metered dose form, for example as a suspension in a propellant such as a halogenated hydrocarbon filled into an aerosol container provided with a metering dispense valve.

It may be advantageous to incorporate an antioxidant, for example ascorbic acid, butylated hydroxyanisole or hydroquinone in the compositions of the invention to enhance their storage life.

Where any of the above compositions are prepared in dosage unit form these may for example contain 0.1–500 μg, e.g. 0.2–100 μg, of active compound according to the invention per unit dosage form. The compositions may if desired incorporate one or more further active ingredients.

A suitable daily dose of an active compound according to the invention may for example be in the range 0.2–1000 μg, e.g. 0.4–200 μg, per day, depending on factors such as the severity of the condition being treated and the age, weight and condition of the subject.

Compounds according to the invention may be prepared by any convenient method, for example one of the following:

A) 5,6-Cis compounds of formula (I) may be prepared by isomerisation of a corresponding 5,6-trans compound, followed if necessary and/or desired by removal of any O-protecting groups. Isomerisation may be effected by, for example, treatment with iodine, with a disulphide or diselenide, or by irradiation with ultraviolet light, preferably in the presence of a triplet sensitiser.

B) 5,6-Trans compounds of formula (I) may be prepared by hydroxylating a corresponding 1-unsubstituted-5,6-trans compound, e.g. a compound (I) having an A= group of the formula

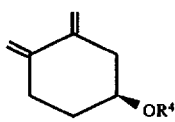

(A-9)

(where $R^4$ is hydrogen or an O-protecting group). Such hydroxylation may be effected using a selenite ester (which may be generated in situ by reaction of selenium dioxide or selenous acid and an alcohol), e.g. as described in GB-A-2038834, or using selenous acid at a pH in the range 3–9, e.g. as described in GB-A-2108506; the contents of both these specifications are incorporated herein by reference. The 1-unsubstituted-5,6-trans compound may, if desired, be prepared by isomerisation of the corresponding 5,6-cis vitamin in situ under the conditions of the hydroxylation reaction, which may be followed by isomerisation and/or removal of O-protecting groups as necessary and/or desired.

C) By reaction of a compound containing a precursor for the desired 17-position side chain in one or more stages and with one or more reactants serving to form the desired side chain, followed if necessary and/or desired by isomerisation and/or removal of O-protecting groups.

Thus, for example, in order to prepare a compound (I) in which $R^1$ and $R^2$ are the same, a compound of general formula (II)

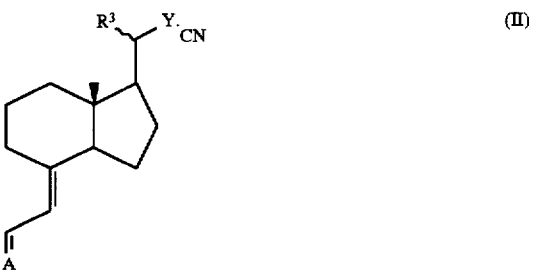

(II)

(where $R^3$, Y and A= are as hereinbefore defined, A= preferably being one of the groups (A-2)–(A-8) in O-protected form) may be reacted with an organo-cerium reagent, e.g. prepared in situ from cerous chloride and an appropriate organometallic compound, e.g. an alkyl/cycloalkyl lithium compound of formula $R^1Li$ (where $R^1$ is as hereinbefore defined), for example as described by Ciganek (J. Org. Chem. (1992), 5, pp 4521–4527).

Compounds of formula (I) in which $R^1$ and $R^2$ are different may, for example, be prepared by reacting a thio-oxime of formula (III)

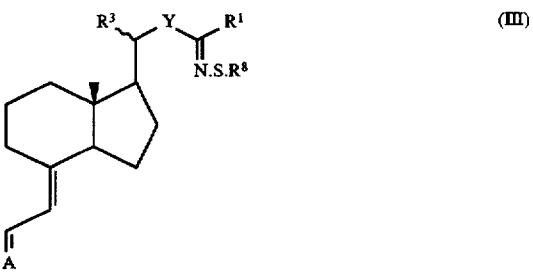

(III)

(where $R^1$, $R^3$, Y and A= are as hereinbefore defined and $R^8$ is an aromatic group, e.g. a carbocyclic aryl group such as phenyl) with an appropriate organometallic compound, for example an alkyl/cycloalkyl lithium compound of formula $R^2Li$ (where $R^2$ is as hereinbefore defined), and reducing the thus-obtained compound of formula (IV)

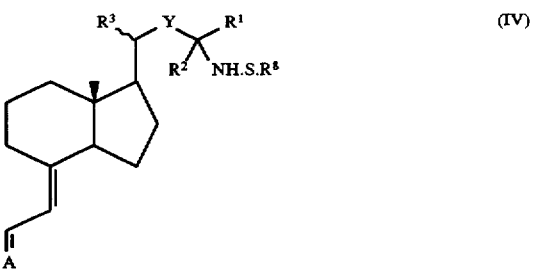

(IV)

(where $R^1$, $R^2$, $R^3$, $R^8$, Y and A= are as hereinbefore defined), e.g. using a metal hydride reducing agent such as sodium borohyride or an inorganic or organic sulphur compound such as hydrogen sulphide, sodium sulphide or a thiol (e.g. a lower alkyl mercaptan such as methanethiol) to remove the $R^8.S$ group and yield a corresponding compound of formula (I) in which R is a hydrogen atom (see J. Org. Chem. (1977), 42, pp 398–399).

Compounds of formula (I) in which R represents a lower alkanoyl, aralkanoyl or aroyl group may be prepared by acylation of a corresponding compound (I) in which R is hydrogen, for example by reaction with an appropriate acyl halide or acid anhydride or with an appropriate acid in the presence of a coupling agent such as N,N'-carbonyl-diimidazole or dicyclohexylcarbodiimide. It will be appreciated that any hydroxyl groups present elsewhere in the molecule, e.g. as substituents of the A= or Y groups, should desirably be in O-protected form during such acylation reactions.

Compounds of formula (I) in which R represents a lower alkyl group may, for example, be prepared by reducing a corresponding compound (I) in which R is a lower alkanoyl group, e.g. using a metal hydride reducing agent such as lithium aluminium hydride. Alternatively a compound (I) in which R represents a hydrogen atom may be subjected to direct alkylation, e.g. by reaction with an alkyl halide, or to reductive amination, e.g. by reaction with an appropriate aldehyde and a reducing agent such as sodium cyanoborohydride.

Compounds of formula (I) in which Y is an alkynylene group may, for example, be prepared by reaction of a compound of formula (V)

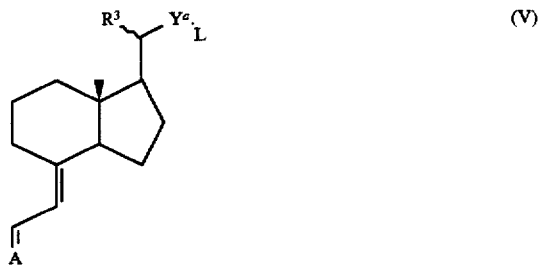

(where $R^3$ and A= are as hereinbefore defined; $Y^a$ is an alkylene group, e.g. containing 1–4 carbon atoms; and L represents a leaving group, for example a sulphonate ester group, e.g. lower alkyl sulphonyloxy such as mesyloxy, lower fluoroalkyl sulphonyloxy such as trifluoromethanesulphonyloxy or aryl sulphonyloxy such as tosyloxy, or a halogen atom such as chlorine, bromine or iodine), with a metallated derivative (e.g. the lithio derivative) of an alkyne of formula (VI)

(where R, $R^1$ and $R^2$ are as hereinbefore defined and n is 0 or an integer, e.g. in the range 1–3).

The thus obtained compound (I) in which Y is the group

(wherein $Y^a$ and n are as hereinbefore defined) may if desired be hydrogenated to convert the triple bond either to a double bond (e.g. using Lindlar catalyst) or to a single bond (e.g. using a noble metal catalyst such as platinum, palladium or homogeneous rhodium or ruthenium). During such hydrogenations the 5,7-diene or 5,7,10(19)-triene system of the compound (I) is preferably protected by formation of a Diels Alder adduct by reaction with a dienophile, e.g. as described in GB-A-2114570 (the contents of which are incorporated herein by reference); preferred dienophiles include diacylazo compounds such as phthalazine diones and phenyl triazoline diones. The Diels Alder adduct may be removed, e.g. by ozonolysis or other oxidative techniques after the hydrogenation.

Compounds of formula (I) in which Y is an alkynylene group carrying a hydroxyl group α to the triple bond may, for example, be prepared by reaction of a compound of formula (VII)

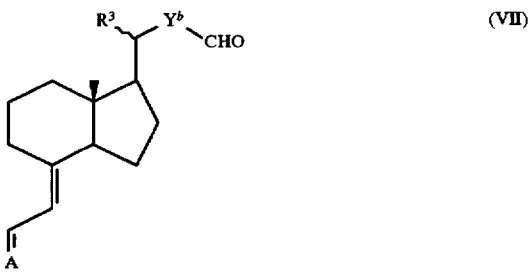

(where $R^3$ and A= are as hereinbefore defined and $Y^b$ is a valence bond or an alkylene group, e.g. containing 1–4 carbon atoms) with a metallated derivative of an alkyne of formula (VI), so as to form a compound (I) in which Y is a group

(wherein $Y^b$ and n are as hereinbefore defined).

Compounds of the formula (VI) may be prepared by subjecting a compound of formula (VIII)

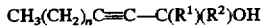

(where n, $R^1$ and $R^2$ are as hereinbefore defined) to a Ritter reaction with a compound of formula $R^a$CN (where $R^a$ represents a hydrogen atom or an appropriate organic group) in the presence of a strong acid, e.g. a mineral acid such as sulphuric acid, thereby leading to formation of a compound (I) in which R represents a group $R^a$.CO—. This group may be removed by hydrolysis to yield a compound (I) in which R represents a hydrogen atom or may be reduced, e.g. as hereinbefore described, to yield a compound (I) in which R represents a group $R^a$.CH$_2$—. Alternatively the hydroxy group of the tertiary carbinol may be displaced by an azido group, e.g. by reaction with hydrazoic acid in the presence of a strong acid, and the azido group reduced to yield a compound (I) in which R represents hydrogen. The internal alkyne may then be isomerized to the terminal position by treatment with the potassium salt of 1,3-propanediamine in 1,3-propanediamine as solvent ("acetylene zipper").

Compounds of formula (II) may, for example, themselves be prepared by reaction of a compound of formula (V) as defined above with, as appropriate, (i) a source of cyanide ion (e.g. an alkali metal cyanide such as sodium or potassium cyanide), (ii) a metallated acetonitrile derivative (e.g. the lithio derivative), or (iii) acrylonitrile, preferably where L is an iodine atom (e.g. by ultrasound-induced chromium-mediated conjugate addition as described by Mourino et al. in *J Org. Chem*, (1993), 58, pp 118–123).

Compounds (II) in which the 17-position side chain terminates in the group —CH:CH.CN may, for example, be prepared from an aldehyde of formula (VI) as defined above by means of a Wittig reaction with an ylid of formula $(R^9)_3$P:CH.CN (where each $R^9$ represents an organic group, e.g. a carbocyclic aryl group such as phenyl) or with a corresponding phosphonate or silyl equivalent.

Compounds of formula (III) may, for example, themselves be prepared by reacting a ketone of formula (X)

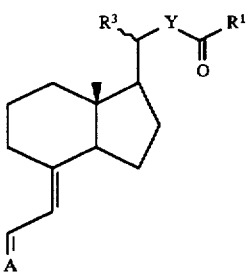

(IX)

(where $R^1$, $R^3$, Y and A= are as hereinbefore defined) with an S-substituted thiolamine of formula $R^8$.S.NH (where $R^8$ is as hereinbefore defined). Such compounds of formula (IX) may be prepared from, for example, an acid of formula (X)

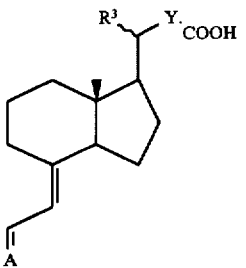

(X)

(where $R^3$, Y and A= are as hereinbefore defined), e.g. by formation of a corresponding acid halide such as the chloride and reaction with an organometallic compound $R^1MX$ (where $R^1$ is as hereinbefore defined; M represents a divalent metal such as copper, zinc or cadmium; and X represents e.g. a halogen atom). Alternatively one may prepare compounds (IX) by reacting a compound of formula (V) above with e.g. (i) an α-metallated derivative such as a lithio derivative of a ketone of formula $CH_3.CO.R^1$ (where $R^1$ is as hereinbefore defined) or with a corresponding enol, or (ii), preferably where L is an iodine atom, a vinyl ketone of formula $CH_2:CH.CO.R^1$ (where $R^1$ is as hereinbefore defined), e.g. by ultrasound-induced chromium-mediated conjugate addition as described by Mourino et al. (op. cit.).

Compounds (X) and esters thereof may also be used to prepare compounds of formula (II) by reaction with ammonia or a metallated derivative thereof, e.g. an alkali metal amide such as lithium amide, to form a corresponding carboxamide which may be converted to a nitrile (II) by mild dehydration, e.g. using tosyl chloride, phosphorus oxychloride in the presence of a base such as pyridine, or trifluoracetic anhydride in the presence of an excess of a base such as pyridine.

Compounds (II) in which Y is α-substituted by a hydroxyl group are conveniently obtained by cyanohydrin formation, for example by reaction of a compound (VII) with hydrogen cyanide. Compounds (II) in which Y is β-substituted by a hydroxyl group may be prepared directly by reaction of a compound (VII) with a metallated (e.g. lithated) derivative of acetonitrile; they may also be prepared indirectly by reaction with a metallated derivative of an ester of acetic acid, followed by conversion of the ester group to a carboxamide group and then to a nitrile group, e.g. as described above.

In general compounds (I) and starting materials therefor in which Y is substituted by a hydroxyl group may be converted to corresponding ether and ester derivatives by standard methods such as are well known in the art. Thus, for example, etherification may be effected by reaction with an appropriate organic halide (e.g. an alkyl iodide) in the presence of an appropriate base (e.g. an alkali metal alkoxide such as potassium t-butoxide), advantageously in the presence of a crown ether such as 18-crown-6. Esterification may be effected by reaction with appropriate acylating agents, such as acyl halides, acid anhydrides and the like.

Useful starting materials for the above compounds of formulae (V), (VII) and (X) include compounds (XI)

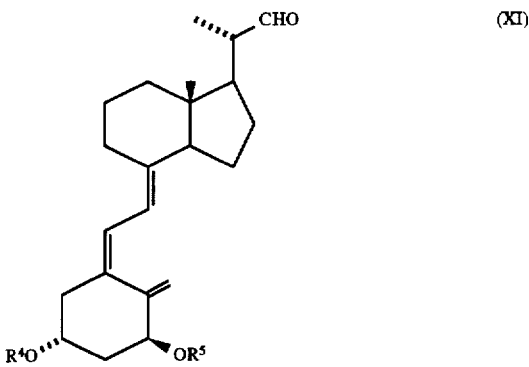

(XI)

(where $R^4$ and $R^5$ are as defined above) and/or 5,6-trans isomers thereof and the corresponding 1-deoxy compounds; such compounds may be obtained through oxidative cleavage (e.g. by ozonolysis) of the 22,23-double bond of vitamin $D_2$, 1α-hydroxy vitamin $D_2$ or O-protected derivatives thereof, these preferably being stabilised by formation of a Diels Alder dienophile adduct, e.g. with sulphur dioxide or a diazacyclo compound, for example as described in GB-A-2114570 (the contents of which are incorporated herein by reference).

Such 20S compounds (XI), optionally still in the form of their dienophile adducts, may be isomerised by, for example, treatment with a mild base, e.g. an inorganic base such as sodium bicarbonate or a tertiary organic base such as 1,4-diazabicyclo [2.2.2]octane ("DABCO") or 1,8-diazabicyclo [5.4.0]undec-7-ene ("DBU"). This yields a mixture of 20R and 20S isomers from which the pure 20R epi-isomer may be isolated chromatographically; alternatively separation of a desired epi-isomer may be delayed until a later stage in the synthesis, up to and including the final step.

Reduction of the aldehyde grouping of a compound (XI) or a corresponding epi-isomer, e.g. using a metal hydride reducing agent such as sodium borohydride, yields a corresponding hydroxymethyl compound, i.e. a compound (V) in which $Y^a$ is $CH_2$ and L is OH. This may be converted to a compound (V) in which L is a leaving group by, for example, conversion to a sulphonate ester (e.g. to a tosylate) followed, if desired, by nucleophilic displacement of the sulphonate group by reaction with a halide salt (e.g. an alkali metal bromide).

Compounds of formula (V) in which A= represents a group (A-9) as hereinbefore defined, $Y^a$ is as hereinbefore defined, and L represents an O-protected hydroxyl group (e.g. in which the hydroxyl group is esterified, for example with a lower alkanoyl group such as acetyl) may be subjected to 1α-hydroxylation as described under (B) above to give compounds (V) in which A= represents a group (A-2) or (A-3) as hereinbefore defined in which $R^5$ represents hydrogen. Such compounds or protected derivatives thereof, e.g. in which $R^5$ is trimethylsilyl, may be hydrogenated (e.g. in the presence of a noble metal catalyst such as tris-triphenylphosphine rhodium chloride) to yield corresponding compounds in which A= represents a group (A-4) or (A-5) as hereinbefore defined, or may be cyclopropanated (e.g. by reaction with methylene iodide in the presence of zinc/copper couple) to yield corresponding compounds in which A= represents a group (A-6) or (A-7) as hereinbefore defined. Where appropriate, the compounds so obtained may be converted to compounds in which $R^5$ is an O-protecting group (e.g. by silylation) and may be hydrolysed (e.g. with base such as potassium hydroxide or potassium carbonate) or reduced (e.g. with lithium aluminium hydride) to remove the side chain ester group to yield useful starting materials (V) in which L represents a hydroxyl group.

19-Nor analogues of compounds of formula (XI) and corresponding 20-hydroxymethyl compounds (i.e. starting materials for compounds (I) in which A= represents a group (A-8) as hereinbefore defined) may be prepared as described by Perlman et al., *Tetrahedron Letters* (1992), 33, pp 2937–2940.

Compounds of formula (V) in which $Y^a$ is e.g. ethylene or trimethylene may, for example, be obtained by reaction of a compound (V) in which $Y^a$ is methylene either (i) with a reagent serving to introduce a one-carbon fragment (e.g. a metal cyanide) and conversion of the group so introduced to a group —$CH_2L$, e.g. by hydrolysing a cyano group to yield a carboxy group or by reducing such a cyano group (e.g. with a metal hydride reducing agent such as diisobutyl aluminium hydride) to yield a carboxaldehyde group, and reducing the carboxy or carboxaldehyde group (e.g. using sodium borohydride or lithium aluminium hydride) to yield a hydroxymethyl group which may in turn be subjected to tosylation and, if desired, nucleophilic displacement as hereinbefore described to effect conversion to a halomethyl group; or (ii) with a metallated derivative of an ester or thioester of acetic acid, with a derivative containing another carbanionic equivalent of acetic acid (e.g. a metallated derivative of acetonitrile), or with a metallated malonate ester (in which last instance the reaction product is partially hydrolysed to yield a monoester which may be decarboxylated by heating to yield a carboxylate ester), reducing the resulting ester or thioester product to an alcohol (e.g. using lithium aluminium hydride), and converting the resulting hydroxyl group to a leaving group, such as a tosylate group or a halogen atom, e.g. as hereinbefore described.

It will be appreciated that the above procedures (i) and/or (ii) may be repeated as needed to yield compounds (V) in which $Y^a$ is a $C_3$–$C_7$ alkylene group. D) By reaction of a compound of formula (I) to modify the substitution pattern about the A= group, followed if necessary and/or desired by isomerisation and/or removal of protecting groups.

Thus for example, compounds (I) in which A= represents a group (A-4) or (A-5) may be prepared by hydrogenation of corresponding compounds in which A= represents (A-2) or (A-3), e.g. using the method of GB-A-1583749. It will be appreciated that such hydrogenation may alternatively be effected at an earlier stage of a reaction sequence, e.g. on a starting material or intermediate of formula (V).

Compounds (I) in which A= represents a group (A-6) or (A-7) may be prepared from corresponding compounds in which A= represents (A-2) or (A-3) (in which $R^4$ is an O-protecting group and $R^5$ is a hydrogen atom or a trimethylsilyl group) by Simmons-Smith methylenation (see e.g. Neef et al., *Tetrahedron Letters* (1991), 32, pp 5073–5076).

Compounds (I) in which A= represents a group (A-8) may, for example, be prepared by cleavage of the 7,8-double bond of an appropriate vitamin D derivative (e.g. a precursor compound (I) in which A= is a group (A-9)), for example by ozonolysis or by successive reaction with potassium permanganate and sodium periodate, followed by Wittig-Horner reaction of the resulting 8-one with an appropriate ring A precursor, e.g. of formula (XII)

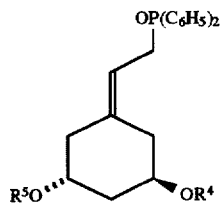

(where $R^4$ and $R^5$ represent O-protecting groups)—see, for example, Perlman et al., *Tetrahedron Letters* (1992), 33, pp 2937–2940.

In general, either 5,6-cis or 5,6-trans geometry may be present at any of the various steps described in (C) and (D) above, although it may be preferred to employ 5,6-trans isomers in the above-mentioned 1α-hydroxylation and 22,23-double bond oxidative cleavage reactions. Conversion of 5,6-trans geometry to 5,6-cis is thus most advantageously effected after introduction of the 1α-hydroxyl group.

It will be appreciated that many of the reaction sequences described above may also be accomplished using appropriate steroid-5,7-dienes (or steroid-5-enes which are convertible into such dienes), followed by conversion of the steroid products into the desired vitamin D analogues, e.g. by irradiation with UV light.

In general, O-protecting groups present at the 1α-and/or 3β- positions may be removed by, for example, conventional methods such as are well documented in the literature. Thus esterifying acyl groups may be removed by basic hydrolysis, e.g. using an alkali metal alkoxide in an alkanol. Etherifying groups such as silyl groups may be removed by acid hydrolysis or treatment with a fluoride salt, e.g. a tetraalkyl ammonium fluoride. The use of such acid-labile but base-stable protecting groups may be of particular advantage during homologation steps to build up a desired side chain, in view of the strongly basic conditions normally employed for such reactions.

The following non-limitative examples serve to illustrate the invention. All temperatures are in °C.

Preparation 1 a) 20α-Acetoxymethyl-1α-hydroxy-3β-triisopropylsilyloxy-9, 10-secopregna-5(E),7-diene [Formula (IV)—A=(A-5), $R^3$=α-$CH_3$, $R^4$=(i-Pr)$_3$ Si , $R^5$=H, L=O.CO.$CH_3$, $Y^a$=$CH_2$]

A solution of tris-triphenylphosphine rhodium chloride (450 mg) in benzene (30 ml) (or in a 1:1 mixture of benzene and ethanol) is stirred under hydrogen until no further uptake is observed. A solution of 20α-acetoxymethyl-1α-hydroxy-3β-triisopropylsilyloxy-9,10-secopregna-5(E), 7,10(19)-triene [Formula (V)—A=(A-3), $R^3$=α-$CH_3$, $R^4$=(i-Pr)$_3$ Si, $R^5$=H, L=O.CO.$CH_3$, $Y^a$ =$CH_2$—as an alternative the corresponding 1α-trimethylsilyl ether may be used] (500 mg) in benzene (30 ml) is added and the mixture stirred under hydrogen until 1 equivalent of hydrogen has been taken up (ca 21 ml). The title compounds are purified by chromatography [the 10(R) and 10(S) isomers may optionally be resolved at this stage] and have UV A$λ_{max}$ ca. 243,251 and 261 nm, with ε=ca. 35,000; 40,000 and 27,000 respectively.

b) 1α,3β-Bis-triisopropylsilylozy-20α-hydroxymethyl-9, 10-secopregna-5(E),7-diene [Formula (V)—A=(A-5), $R^3$=α-$CH_3$, $R^4$=$R^5$=(i-Pr)$_3$ Si, L=OH, $Y^a$=$CH_2$]

The diene from (a) above (ca 500 mg) in dichloromethane (2 ml) is treated with chlorotriisopropylsilane (250 mg) and imidazole (350 mg) and the mixture stirred overnight at room temperature. After work up the crude bis-silyl ether is dissolved in tetrahydrofuran (10 ml), treated with lithium aluminium hydride (100 mg) and stirred at room temperature for 1–2 hours. After decomposition of the excess lithium aluminium hydride (careful addition of saturated aqueous sodium sulphate) the reaction mixture is worked up to afford the title alcohol.

Preparation 2

1α,3β-Bis-triisoipropylsilyloxy-20α-hydroxymethyl-9,10-secopregna-5(Z),7-diene [Formula (V)—A=(A-4), $R^3$=α-$CH_3$, $R^4$=$R^5$=(i-Pr)$_3$ Si, L=OH, $Y^a$=$CH_2$]

The 5(E)-triene starting material in Preparation 1(a) is photoisomerised in benzene in the presence of phenazine by irradiation for 1 hour, to yield the corresponding 5(Z)-triene. This product is hydrogenated as described in Preparation 1(a) and silylated and de-acetylated as described in Preparation 1(b) to give the title compound. UV $\lambda_{max}$ ca. 243, 251 and 261 nm with ε=ca. 35,000; 40,000 and 27,000 respectively.

The epi (i.e. 20β-hydroxymethyl) compounds corresponding to the products of Preparations 1 and 2 are prepared by the same procedures starting with the 20-epi compound 20β-acetoxymethyl-1α-hydroxy-3⊖-triisopropylsilyloxy-9,10-secopregna-5(E),7,10(19)-triene [Formula (V)—A=(A-3), $R^3$=β-$CH_3$, $R^4$=(i-Pr)$_3$ Si, $R^5$=H, L=O.CO.$CH_3$, $Y^a$=$CH_2$]. This is itself prepared by isomerisation of the 20-aldehyde obtained by ozonolysis of the sulphur dioxide adduct of vitamin $D_2$ followed by reduction and 1α-hydroxylation of the 20-epi aldehyde.

Preparation 3 a) 20α-Acetoxymethyl-1αhydroxy-3β-triisonropylsilyloxy-10-spirocyclopropyl-9,10-secopregna-5(E),7-diene [Formula (V)—A=(A-7), $R^3$=α-$CH_3$, $R^4$=(i-Pr)$_3$ Si, $R^5$=H, L=O.CO.$CH_3$, $Y^a$=$CH_2$]

A mixture of zinc/copper couple (1.08 g) and diiodomethane (0.9 ml) in ether (6 ml) is heated under reflux with stirring for 40 minutes. A solution of 20α-acetoxymethyl-1α-hydroxy-3β-triisopropylsilyloxy-9,10-secopregna-5(E), 7,10(19)-triene [Formula (V)—A=(A-3), $R^3$=α-$CH_3$, $R^4$=(i-Pr)$_3$ Si, $R^5$=H, L=O.CO.$CH_3$, $Y^a$=$CH_2$ —as an alternative the corresponding 1α-trimethylsilyl ether may be used] (ca. 500 mg) in ether (9 ml) is added, and the mixture is stirred and heated under reflux until most of the starting material has disappeared (TLC control: usually about 4 hours for the 1α-trimethylsilyl ether, less for the 1α-hydroxy compound). The reaction mixture is filtered, the solvent removed and the product chromatographed to remove the remaining diiodomethane. The title compound has UV $\lambda_{max}$ ca. 246, 253 and 263 nm, with ε=ca. 29,000; 36,000 and 25,000 respectively.

b) 1α,3β-Bis-triisopropylsilyloxy-20α-hydroxymethyl-10-spirocyclopropyl-9,10-secopregna-5(E),7-diene [Formula (V)—A=(A-7), $R^3$=α-$CH_3$, $R^4$=$R^5$=(i-Pr)$_3$ Si, L=OH, $Y^a$=$CH_2$]

The diene from (a) above (ca. 500 mg) in dichloromethane (2 ml) is treated with chlorotriisopropylsilane (250 mg) and imidazole (350 mg) and the mixture stirred overnight at room temperature. After work up the crude bis-silyl ether is dissolved in tetrahydrofuran (10 ml), treated with lithium aluminium hydride (100 mg) and stirred at room temperature for 1–2 hours. After decomposition of the excess lithium aluminium hydride (careful addition of saturated aqueous sodium sulphate) the reaction mixture is worked up to afford the title alcohol.

Preparation 4

1α,3β-Bis-triisopropylsilyloxy-20αhydroxymethyl-10-spirocyclopropyl-9,10-secopregna-5(Z),7-diene [Formula (V)—A=(A-6) $R^3$=α-$CH_3$, $R^4$=$R^5$=(i-Pr)$_3$ Si, L=OH, $Y^a$=$CH_2$]

The procedure of Preparation 3(a) is repeated starting from the corresponding 5(Z)-triene, prepared by photoisomerization of the 5(E)-triene as described in Preparation 2; the reaction of the 5(Z)-triene is somewhat slower than that of the 5(E)-triene. Silylation and de-acetylation as described in Preparation 3(b) gives the title compound. UV $\lambda_{max}$ ca. 246, 253 and 263 nm with ε=ca. 29,000; 36,000 and 25,000 respectively.

Preparation 5

1α,3β-Bis-t-butyldimethylsilyloxy-20β-hydroxthyl-19-nor-9,10-secopregna-5(E),7-diene [Formula (V)—A=(A-8), $R^3$=β-$CH_3$, $R^4$=$R^5$=t-Bu(Me)$_2$Si, L=OH, $Y^a$=$CH_2$]

1α,3β-Bis-t-butyldimethylsilyloxy-20α-formyl-19-nor-9,10-secopregna-5,7-diene [Formula (VII)—A=(A-8), $R^1$=α-CH3, $R^4$=$R^5$=t-Bu(Me)$_2$Si, $Y^b$=valence bond] obtained as in Tetrahedron Lett. (1992), 33, p 2937, (about 1.5g) is dissolved in benzene (15 ml) and methanol (15 ml) and isomerised by storage overnight with DBU (400 μl) at 00. The mixture of normal (20α-formyl) and epi (20β-formyl) aldehydes may be resolved by chromatography (silica eluted with 15% benzene in hexane) before or after reduction of the aldehyde (ca 1 g) in benzene (30 ml) by dropwise treatment with sodium borohydride, (400 mg) in ethanol (15 ml) at 0°, whereafter the reaction mixture is stirred at 0° for a further 0.5 hour. After work up the product is resolved by chromatography (silica gel eluting with benzene or ether in hexane) to yield the title compound.

Preparation 6 a) 1α,3β-Bis-triisopropylsilyloxy-23-nor-9,10-seco-chola-5 (E),7,10,19-trienic acid, nitrile (mixture of 20-normal and 20- epi isomers) [Formula (II)—A=(A-3), $R^3$=α- and β-$CH_3$, $R^4$=$R^5$=(i-Pr)$_3$ Si, $Y^a$=$CH_2$]

A solution of 1α,3β-bis-triisopropylsilyloxy-20(α,β)-tosyloxymethyl-9,10-secopregna-5(E),7,10(19)-triene [Formula (V)—A=(A-3), $R^3$=α,β-$CH_3$, $R^4$=$R^5$=(i-Pr)$_3$Si, L=O.tosyl, $Y^a$=$CH_2$] (1 g) in dimethylsulphoxide (5 ml) containing potassium cyanide (390 mg) was heated at 90° for 2 hours, and the product was extracted (diethyl ether), washed and purified by column chromatography to give the title nitrile (748 mg). UV (Et$_2$O) $\lambda_{max}$ 267, $\lambda_{min}$ 229 nm; NMR (CCl$_4$) δ5.36–6.13 (ABq, 6,7-H's), 4.83 (bs, 19-H's), 4.13–4.46 (m, 1,3-H's), 0.53 (s, 18-H's).

b) 1α,3β-Bis-triisopropylsilyloxy-23-nor-9,10-seco-chola-5 (E),7,10,19-trienic carboxaldehyde, (mixture of 20- normal and 20- epi isomers) [Formula (V)—A=(A-3), $R^3$=α- and β-$CH_3$, $R^4$=$R^5$=(i-Pr)$_3$ Si, L=CHO, $Y^a$=$CH_2$]

The nitrile from (a) above (480 mg) in hexane (3 ml) was cooled to −78° and treated with diisobutylaluminium hydride (1.4 ml of a 1M solution in heptane). The mixture was stirred at 0° for 1 hour, treated with ether and saturated ammonium chloride solution, and the product isolated by extraction into ether. The crude product had UV (Et$_2$O) $\lambda_{max}$ 270, $\lambda_{min}$ 229 nm; IR (CCl$_4$) $v_{max}$ 1730 cm$^{-1}$; NMR (CCl$_4$) δ 10.6 (bs, CHO), 5.53–6.23 (ABq, 6,7-H's), 4.76 (bs, 19-H's), 4.16–4.43 (m, 1,3-H's), 56 (s, 18-H's).

c) 1α,3β-Bis-triisopropylsilyloxy-20(α,β)-(2-hydroxymethyl)-9,10-secopregna-5(E),7,10,19-triene [Formula (V)—A=(A-3), $R^3$=α- and β-$CH_3$, $R^4$=$R^5$=(i-Pr)$_3$ Si, L=OH, $Y^a$=(CH$_2$)$_2$]

The aldehyde from (b) above (440 mg) in benzenle (10 ml) was treated at 0° with a solution of sodium borohydride (105 mg) in ethanol (10 ml) followed by stirring at room temperature for 45 minutes. After work up the product was purified by chromatography to give the title compound (380 mg). UV (Et$_2$O) $\lambda_{max}$ 269, $\lambda_{min}$ 228 nm; IR (CCl$_4$) $v_{max}$ 3500–3700 cm$^{-1}$; NMR (CCl$_4$) δ 5.53–6.3 (ABq, 6,7-H's), 4.73 (bs, 19-H's), 4.16–4.43 (m, 1,3-H's), 0.56 (s, 18-H's).

The isomers (at C-20) were resolved by careful chromatography of 1.2 g of mixture on silica gel developed with 30% benzene in hexane. The 20β-(epi) isomer (145 mg) was less polar and eluted first followed by a mixture of isomers and then the 20α-(normal) isomer (360 mg).

d) 1α,3β-Bis-triisoropylsilyloxy-20α-(2-bromoethyl)-9,10-secopregna-5(E),7,10(19)-triene [Formula (V)—A=(A-3), $R^3$=α-$CH_3$, $R^4$=$R^5$=(i-Pr)$_3$Si, L=Br, $Y^a$=$(CH_2)_2$]

The normal alcohol from (c) above (200 mg) was stirred at room temperature for 2 hours in dichloromethane (5 ml) containing p-toluenesulphonyl chloride (110 mg) and pyridine (243 μl). Sodium bicarbonate (20 ml of a saturated solution) was added, the stirring continued for a further 2 hours, and the reaction mixture worked up. The crude tosylate was dissolved in acetonitrile (6.6 ml) and dichloromethane (6.6 ml) containing lithium bromide (317 mg) and 1.8 bis-dimethylaminonaphthalene ("proton sponge" 40 mg) and the mixture heated under reflux at 80° for 30 minutes. The mixture was then cooled and worked up to give the title bromide (261 mg, purified by chromatography). UV ($Et_2O$) $\lambda_{max}$ 267, $\lambda_{min}$ 228 nm; NMR ($CCl_4$) δ 5.43–6.16 (ABq, 6,7-H's), 4.76 (bs, 19-H's), 4.14–4.45 (m, 1,3-H's), 3.16 (m, $Cl_2Br$), 0.5 (s, 18-H's).

Preparation 7 a) 1α,3β-Bis-triisopropylsilyloxy-20α-bromomethyl-9,10-secopregna-5(E),7-diene [Formula (V)—A=(A-5), $R^3$=α-$CH_3$, $R^4$=$R^5$=(i-Pr)$_3$ Si, L=Br, $Y^a$=$CH_2$]

This compound is prepared from the product of Preparation 1 following the procedure of Preparation 6(d).

b) 1α,3β-Bis-triisopropylsilyloxy-20α-bromomethy-9,10-secopregna-5(Z),7-diene [Formula (V)—A=(A-4), $R^3$=α-$CH_3$, $R^4$=$R^5$=(i-Pr)$_3$ Si, L=Br, $Y^a$=$CH_2$]

This compound is prepared from the product of Preparation 2 following the procedure of Preparation 6(d).

c) 1α,3β-Bis-triisopropylsilyloxy-20α-bromoethyl-10-spirocyclopropyl-9,10-secopregna-5(E),7-diene [Formula (V)—A=(A-7), $R^3$=α-$CH_3$, $R^4$=$R^5$=(i-Pr)$_3$ Si, L=Br, $Y^a$=$CH_2$]

This compound is prepared from the product of Preparation 3 following the procedure of Preparation 6(d).

d) 1α,3β-Bis-triisopropylsilyloxy-20α-bromoethyl-10-spirocyclopropyl-9,10-secopregna-5(Z),7-diene [Formula (V)—A=(A-6), $R^3$=α-$CH_3$, $R^4$=$R^5$=(i-Pr)$_3$ Si, L=Br, $Y^a$=$CH_2$]

This compound is prepared from the product of Preparation 4 following the procedure of Preparation 6(d).

e) 1α,3β-Bis-t-butyldimethylsilyloxy-20β-bromomethyl-12-nor-9,10-secopregna-5(E),7-diene [Formula (V)—A=(A-8), $R^3$=β-$CH_3$, $R^4$=$R^5$=(i-Pr)$_3$ Si, L=Br, $Y^a$=$CH_2$]

This compound is prepared from the product of Preparation 5 following the procedure of Preparation 6(d).

Preparation 8 a) 1α,3β-Bis-triisopropylsilyloxy-20α-bromoethyl-9,10-secopregna-5(E),7-diene [Formula (V)—A=(A-5), $R^3$=α-$CH_3$, $R^4$=$R^5$=(i-Pr)$_3$ Si, L=Br, $Y^a$=$(CH_2)_2$]

The title compound is prepared from the product of Preparation 7(a) following the procedures of Preparation 6(a)–(d).

b) 1α,3β-Bis-triisopropylsilyloxy-20α-bromoethyl-9,10-secopregna-5(Z),7-diene [Formula (V)—A=(A-4), $R^3$=α-$CH_3$, $R^4$=$R^5$=(i-Pr)$_3$ Si, L=Br, $Y^a$=$(CH_2)_2$]

The title compound is prepared from the product of Preparation 7(b) following the procedures of Preparation 6(a)–(d).

c) 1α,3β-Bis-triisopropylsilyloxy-20α-bromoethyl-10-spirocyclopropyl-9,10-secopreana-5(E),7-diene [Formula (V) A=(A-7), $R^3$=α-$CH_3$, $R^4$=$R^5$=(i-Pr)$_3$ Si, L=Br, $Y^a$=$(CH_2)_2$]

The title compound is prepared from the product of Preparation 7(c) following the procedures of Preparation 6(a)–(d).

d) 1α,3β-Bis-triisopropylsilyloxy-20α-bromoethyl-10-spirocyclopropyl-9,10-secopregna-5(Z),7-diene [Formula (V)—A=(A-6), $R^3$=α-$CH_3$, $R^4$=$R^5$=(i-Pr)$_3$ Si, L=Br, $Y^a$=$(CH_2)_2$]

The title compound is prepared from the product of Preparation 7(d) following the procedures of Preparation 6(a)–(d).

e) 1α,3β-Bis-t-butyldimethylsilyloxy-20β-bromoethyl-19-nor-9,10-secopregna-5,7-diene [Formula (V)—A=(A-8), $R^3$=β-$CH_3$, $R^4$=$R^5$=(i-Pr)$_3$ Si, L=Br, $Y^a$=$(CH_2)_2$]

The title compound is prepared from the product of Preparation 7(e) following the procedures of Preparation 6(a)–(d).

Preparation 9 a) 1α,3β-Bis-triisopropylsilyloxy-24-carbamoyl-24-homo-9,10-secochola-5(E),7,10(19),22(E), 24(E)-pentaene [$NH_2$ amide of acid of formula (X)—A=(A-3), $R^3$=α-$CH_3$, $R^4$=$R^5$=(i-Pr)$_3$ Si, Y=CH=CH—CH=CH]

Lithium aluminium hydride (10 ml of a 1M solution in ether) was stirred at room temperature under an atmosphere of ammonia for 30 minutes. The resulting suspension was treated with 1α,3β-bis-triisopropylsilyloxy-24-ethoxycarbonyl-24-homo-9,10-secochola-5(E), 7,10(19) ,22(E),24(E)-pentaene [ethyl ester of acid of formula (X)—A=(A-3), $R^3$=α-$CH_3$, $R^4$=$R^5$=(i-Pr)$_3$ Si, Y=CH=CH—CH=CH] (250 mg) in ether (1 ml) and the mixture was stirred for 10 hours at room temperature. The reaction mixture was then cooled to 0°, treated (caution!) with aqueous ethanol (3 ml, 70%), diluted with ether and dried over sodium sulphate. Purification by column chromatography gave the title compound (180 mg). UV ($Et_2O$) $\lambda_{max}$ 260 nm; IR $v_{max}$ ($CDCl_3$) 3520–3000, 1670, 1630, 1580 $cm^{-1}$; NMR ($CDCl_3$) δ 0.63 (s, 18-H's), 3.8–4.7 (m, 1,3-H's), 4.7–5.0 (bs, 19-H's), 5.3–7.3 (m, 6,7,22,23,24,24a-H's).

b) 1α,3β-Bis-triisopropylsilyloxy-24-cyano-24-homo-9,10-secochola-5(E),7,10(19),22(E),24(E)-pentaene [Formula (II)—A=(A-3), $R^3$=α-$CH_3$, $R^4$=$R^5$=(i-Pr)$_3$ Si, Y=CH=CH—CH=CH]

Trifluoroacetic anhydride (54 μl) was added dropwise to a stirred, ice-cooled solution of the amide from (a) above in anhydrous dioxan (540 μl) containing pyridine (150 μl). The mixture was stirred for 1 hour at room temperature, diluted with ether, washed successively with water, aqueous hydrochloric acid, saturated aqueous sodium bicarbonate and brine and then dried. The solvents were removed in vacuo and the product was isolated by chromatography to give the title compound (115 mg). UV ($Et_2O$) $\lambda_{max}$ 260 nm; IR $v_{max}$ ($CDCl_4$) 2100, 1630 $cm^{-1}$; NMR ($CDCl_3$) δ 0.56 (s, 18-H's), 3.8–4.6 (m, 1,3-H's), 4.6–5.0 (bs, 19-H's), 5.3–7.3 (m, 6,7,22,23, 24,24a-H's).

EXAMPLE 1 a) 1α,3β-Bis-triisopropylsilyloxy-9,10-secochola-5(E),7,10 (19)-triene-24-carbonitrile [Formula (II)—A=(A-3), $R^3$=α-$CH_3$, $R^4$=$R^5$=(i-Pr)$_3$ Sii, Y=$(CH_2)_3$]

A solution of 1α,3β-bis-triisopropylsilyloxy-24-tosyloxy-9,10-secochola-5(E),7,10(19)-triene, generated in situ by tosylation of the corresponding 24-ol (480 mg, prepared as described in Example 2(c) of WO 93/09093), in dimethyl sulphoxide (2.5 ml) containing potassium cyanide (220 mg) was heated at 90° for 50 minutes, cooled and extracted with ethyl acetate. The thus-obtained product was purified by column chromatography to yield the title compound (320 mg). UV ($Et_2O$) $\lambda_{max}$ 267, $\lambda_{min}$ 236 nm; NMR ($CCl_4$) δ 5.53–6.3 (ABq, 6,7-H's), 4.8 (s, 19-H's), 0.50 (s, 18-H's).

b) 25-Amino-1α,3β-bis-triisopropylsilyloxy-9,10-secocholesta-5(E),7,10(19)-triene [Formula (I)—A=(A-3), R=H, R¹=R²=CH₃, R³=α-CH₃, R⁴=R⁵=(i-Pr)₃ Sii, Y=(CH₂)₃]

Tetrahydrofuran (2 ml) was added to cerous chloride (639 mg) at 0°. The resulting solution was stirred at room temperature for 15 minutes, cooled to −70°, treated with methyl lithium (1.85 ml of a 1.6M solution in tetrahydrofuran) and stirred briefly at −70°. The nitrile from (a) above (320 mg) in tetrahydrofuran (2.5 ml) was added at −70° to the thus-prepared alkyl cerium reagent and the reaction mixture was stirred for 1 hour at −70°, briefly warmed to room temperature, cooled to −700°, quenched with concentrated aqueous ammonia (2 ml) and filtered through Celite, which was thereafter washed with tetrahydrofuran and diethyl ether. The product was isolated from the combined organic phases and purified by chromatography (alumina) to give the title compound (235 mg). UV (Et₂O) $\lambda_{max}$ 268, $\lambda_{min}$ 228 nm; NMR (CDCl₃) δ 5.58–6.3 (ABq, 6,7-H's), 4.83 (s, 19-H's), 0.53 (s, 18-H's).

c) 25-Amino-1α,3β-bis-triisopropylsilyloxy-9,10-secocholesta-5(Z),7,10(19)-triene [Formula (I)—A=(A-2), R=H, R¹=R²=CH₃ R³=-CH₃, R⁴=R⁵=(i-Pr)₃ SiSi, Y=(CH₂)₃]

A solution of the 5(E) compound from (b) above (188 mg) in benzene (25 ml) containing phenazine (98 mg) was irradiated for 50 minutes. The product was worked up and purified by TLC to give the title compound (140 mg). UV (Et₂O) $\lambda_{max}$ 260, $\lambda_{min}$ 222 nm; NMR (CDCl₃) δ 5.66–6.2 (ABq, 6,7-H's), 4.7–5.03 (d, 19-H's), 0.50 (s, 18-H's).

d) 25-Amino-1α,3β-dihydroxy-9,10-secocholesta-5(Z),7,10(19)-triene [Formula (I)—A=(A-2), R=H, R¹=R²=CH₃ R³=-CH₃, R⁴=R⁵=H, Y=(CH₂)₃]

The bis-silyl ether from (c) above (60 mg) in tetrahydrofuran (0.556 μl) was desilylated by treatment with tetrabutylammonium fluoride (0.556 μl of a 1M solution in tetrahydrofuran) for 3 hours. The product was extracted into chloroform, which was then washed twice with water, dried and evaporated in vacuo. The thus-obtained product was purified by two successive TLC's to yield the title compound (10.6 mg). UV (EtOH) $\lambda_{max}$ 264, $\lambda_{min}$ 228nm; NMR (CDCl₃) δ 5.66–6.23 (ABq, 6,7-H's), 4.8–5.13 (d, 19-H's), 1.1–1.2 (d, 26,27-H's), 0.50 (s, 18-H's) ; IR (CDCl₃) $v_{max}$ 3600–3350 cm⁻¹ (OH,NH)

EXAMPLE 2 a) 1α,3β-Bis-triisopropylsilyloxy-22,23-bisnor-9,10-secochola-5(E),7,10(19)-triene-24-carbonitrile, mixture of 20R and 20S isomers [Formula (II)—A=(A-3), R³=α-and β-CH₃ (~1:1), R⁴=R⁵=(i-Pr)₃ Sii, Y=CH₂]

A solution of 1α,3D-bis-triisopropylsilyloxy-20(α,β)-tosyloxymethyl-9,10-secopregna-5(E),7,10(19)-triene [Formula (V)—A=(A-3), R³=α- and β-CH₃, R⁴=R⁵=(i-Pr)₃ Sii, Yᵃ=CH₂, L=tosyloxy] (1 g) in dimethylsulphoxide (5 ml) containing potassium cyanide (390 mg) was heated at 90° for 2 hours. The product was extracted with diethyl ether, washed and purified by column chromatography to give the title compound (748 mg). UV (Et₂O) $\lambda_{max}$ 267, $\lambda_{min}$ 229 nm; NMR (CCl₄) δ 5.36–6.13 (ABq, 6,7-H's), 4.83 (bs, 19-H's), 4.13–4.46 (m, 1,3-H's), 0.53 (s, 18-H's).

b) 25-Amino-1α,3β-bis-triisopropylsilyloxy-23,24-bisnor-9,10-secocholesta-5(E),7,10(19)-triene, mixture of 20R and 20S isomers [Formula (I)—A=(A-3), R=H, R¹=R²=CH₃, R³=α- and β-CH₃ (~1:1), R⁴=R⁵=(i-Pr)₃ Sii, Y=CH₂]

A solution of cerous chloride (492 mg, 2 mM) in tetrahydrofuran (2.5 ml) was stirred at room temperature for 1 hour, cooled to −78°, treated with methyl lithium (2 mM in hexane), and stirred for a further 30 minutes at −78°. A solution of the product from (a) above (262 mg) in tetrahydrofuran (1.5 ml) was added, and the reaction mixture was stirred at −78° for 1.5 hours, allowed to warm to room temperature over 2 hours, cooled again to −78°, and worked up as in Example 1(b) to give the title compound (170 mg). UV (Et₂O) $\lambda_{max}$ 269 nm; NMR (CDCl₃) δ 5.53–6.33 (ABq, 6,7-H's), 4.76 (s, 19-H's), 0.53 (s, 18-H's).

c) 25-Amino-1α,3β-bis-triisopropylsilyloxy-23,24-bisnor-9,10-secocholesta-5(Z),7,10(19)-triene, mixture of 20R and 20S isomers [Formula (I)—A=(A-2), R=H, R¹=R²=CH₃, R³=α- and β-CH₃ (~1:1), R⁴=R⁵=(i-Pr)₃ Sii, Y=CH₂]

A solution of the product from (b) above (170 mg) in benzene (20 ml) containing phenazine (80 mg) was photoisomerised and worked up as in Example 1(c) to give the title compound (90 mg). UV (Et₂O) $\lambda_{max}$ 262 nm; NMR (CDCl₃) δ 5.63–6.06 (ABq, 6,7-H's), 4.9–5.2 (each s, 19-H's), 1.4 (s, gem CH₃'s), 0.50 (s, 18-H's).

d) 25-Amino-1α,3β-dihydroxy-23,24-bisnor-9,10-secocholesta-5(Z),7,10,(19)-triene, mixture of 20R and 20S isomers [Formula (I)—A=(A-2), R=H, R¹=R²=CH₃, R³=α- and β-CH₃ (~1:1), R⁴=R⁵=H, Y=CH₂]

A solution of the product from (c) above (90 mg) in tetrahydrofuran (0.5 ml) was stirred with tetrabutylammonium fluoride (0.38 ml of a 1M solution in tetrahydrofuran) overnight. Monitoring by TLC showed that unchanged starting material remained, so the mixture was treated with further tetrabutylammonium fluoride (0.65 ml) and stirred for a further 3 hours. The mixture was worked up and the product was isolated and purified by column chromatography on alumina (twice) to give the title compound. UV (EtOH) $\lambda_{max}$ 263 nm; IR (CDCl₃) $v_{max}$ 3600–3340 cm⁻¹ (OH, NH); NMR (CDCl₃) δ 5.56–6.23 (ABq, 6,7-H's), 4.9–5.23 (each s, 19-H's), 1.03, 1.23, 1.36 (m, 21-CH₃, gem CH₃'s), 0.56 (s, 18-H's)

EXAMPLE 3 a) 25-Acetamido-1α,3β-bis-triisopropylsilyloxy-9,10-secocholesta-5(Z),7,10(19)-triene [Formula (I)—A=(A-2), R=CH₃CO, R¹=R²=CH₃, R³=α-CH₃, R⁴=R⁵=(i-Pr)₃ Sii, Y=(CH₂)₃]

A solution of the product from Example 1(c) (60 mg) in methylene chloride (1 ml) was treated with acetic anhydride (290 μl) and pyridine (290 μl) and the resulting mixture was stirred at room temperature for 3.5 hours then treated with aqueous sodium bicarbonate. After a further 2 hours the mixture was worked up and the product was isolated by TLC to give the title compound (42 mg). UV (Et₂O) $\lambda_{max}$ 261, $\lambda_{min}$ 225 nm; IR (CCl₄) 3420, 3300 (NH), 1670 (C=O) cm⁻¹; NMR (CCl₄) δ 5.96–6.1 (ABq, 6,7-H's), 4.76, 5.06 (each s, 19-H's), 1.76 (s, COCH₃), 1.23 (s, gem CH₃'s), 0.58 (s, 18-H's).

b) 25-Acetamido-1α,3β-dihydroxy-9,10-secocholesta-5(Z), 7,10(19)-triene [Formula (I)—A=(A-2), R=CH₃CO R¹=R²=CH₃, R³=α-CH₃, R⁴=R⁵=H, Y=(CH₂)₃]

A solution of the bis-silyl ether from (a) above (42 mg) in tetrahydrofuran (0.37 ml) was treated with tetrabutylammonium fluoride (0.36 ml of a 1M solution in tetrahydrofuran). The resulting mixture was stirred at room temperature for 2 hours, treated with further tetrabutylammonium fluoride solution (0.1 ml), stirred for 3 hours and worked up. The product was isolated by TLC to give the title compound (20.2 mg). UV (EtOH) $\lambda_{max}$ 263, $\lambda_{min}$ 225 nm; IR (CDCl₃) 3420, 3600 (NH, OH), 1660 (C=O) cm⁻¹; NMR (CDCl₃) δ 5.7–6.3 (ABq, 6,7-H's), 4.8, 5.06 (each s, 19-H's), 1.83 (s, COCH₃), 1.23 (s, gem CH3's), 0.83, 0.9 (d, 21-H's), 0.58 (s, 18-H's).

EXAMPLE 4 a) 1α,3β-Bis-triisopropylsilyloxy-20-epi-9,10-secochola-5 (E),7,10(19)-triene-24-carbonitrile [Formula (II) A=(A-3-, R³=β-CH₃, R⁴=R⁵=(i-Pr)₃ Si, Y=(CH₂)₃]

Acetonitrile (0.32 ml) in tetrahydrofuran (2 ml) was added dropwise at −78° to a solution of butyl, lithium (3.75 ml) of a 1.6M solution in hexane) and tetrahydrofuran (4 ml). After 50 minutes storage at 78° all but a 0.38 mMole portion of the solution (presumed to contain a total of 6 mMoles) was expelled and the remaining portion treated with a solution of 1α,3β-bis-triisopropylsilyoxy-20β-bromoethyl-9,10-secopregna-5(E), 7,10(19)-triene [Formula (V)—A=(A-3),$R^3$=β-$CH_3$ $R^4$=$R^5$=(i-Pr)$_3$ Si, L=Br, Y=$(CH_2)_2$] (100 mg) in tetrahydrofuran (2.05 ml). After 1.5 hours storage at −780° (starting material no longer present by TLC), the reaction mixture was treated with aqueous ammonium chloride and the product extracted into ether. The crude product was combined with similar material from a second reaction (carried out as above on 172 mg bromide) and the product purified by chromatography to give the title compound (193 mg). (UV (Et$_2$O) $\lambda_{max}$ 269, $\lambda_{min}$ 228 nm; NMR (CCl$_4$) δ 0.53 (s,18-H's), 4.8 (s, 19-H's), 5.56–6.3 (ABq, 6,7-H's).

b) 25-Amino-1α,3β-bis-triisopropylsilylozy-20-epi-9,10-secocholesta-5(E),7,10(19)-triene [Formula (I)—A=(A-3), R=H, $R^1$=$R^2$=$CH_3$, $R^4$=$R^5$=(i-Pr)$_3$ Si, Y=$(CH_2)_3$]

A solution of cerous chloride in tetrahydrofuran was treated at 0° with sufficient methyl lithium (1.8 ml of a [?M] solution in hexane) to produce a persistent yellow colour. The solution was cooled to −78°, a further portion of methyl lithium (1.35 ml) was added and the mixture was kept at −78° for 40 minutes to complete formation of the organocerium reagent. The nitrile from (a) above (196 mg in 3 ml tetrahydrofuran) was added at −78° and the reaction mixture was stirred at that temperature for an additional 60 minutes, warmed to −40°, cooled to −78° and treated with ammonium hydroxide. The crude product was filtered through celite (methylene chloride/diethyl ether) and purified by chromatography to give the title compound (120 mg). UV (Et$_2$O), $\lambda_{max}$ 269, $\lambda_{min}$ 228 nm; NMR (CCl$_4$) δ 0.53 (s, 18-H's), 4.13–4.66 (bm,1,3-H's), 4.9 (s, 19-H's), 5.66–6.46 (ABq,6, 7-H's), 6.46 (bs, NH's, exchanges with D$_2$O).

c) 25-Amino-1α,3β-bis-triisopropylsilyloxy-20-epi-9-secocholesta-5(Z),7,10(19)-triene [Formula (I)—A=(A-2), R=H,$R^1$=$R^2$=$CH_3$, $R^3$=β-$CH_3$ $R^4$=$R^5$=(i-Pr)$_3$ Si, Y=$(CH_2)_3$]

The amine from (b) above (80 mg) was photoisomerised by irradiation for 40 minutes in solution in benzene (10.6 ml) contained phenazine (42 mg). Chromotography afforded the title compound (50 mg). UV (Et$_2$O) $\lambda_{max}$ 263, $\lambda_{min}$ 226 nm; NMR (CDCl$_3$) δ 0.50 (s, 18-H's), 4.06–4.6 (bm, 1,3-H's), 4.6, 4.76 (ea. s, 19-H's), 5.53–6.2 (ABq, 6,7-H's), 6.2 (bs, NH's, exchanges with D$_2$O).

d) 25-Amino-1α,3β-dihydroxy-20-epi-9,10-secocholesta-5 (Z),7,10(19)-triene [Formula (I)—A=(A-2), R=H, $R^1$=$R^2$= $CH_3$, $R^3$=β-$CH_3$, $R^4$=$R^5$=H, Y=$(CH_2)_3$]

The silyl ether (52 mg) from (c) above was desilyated by treatment with tetrabutylammonium fluoride (350 µl) in tetrahydrofuran (350 µl) overnight at room temperature. Chromatography gave the title compound (8.7 mg). UV (EtOH) $\lambda_{max}$ 263-4, $\lambda_{min}$ 225-6 nm; IR (CHCl$_3$) 3400, 3600cm$^{-1}$ (OH, NH); NMR (CDCl$_3$) δ 0.53 (s, 18-H's), 0.86, 0.76 (d 21-H's), 2.03 (bs, NH's, exchanges with D$_2$O), 4.06–4.46 (bm, 1,3-H's), 4.9, 5.23 (ea. s, 19-H's), 5.76–6.4 (ABq, 6,7-H's).

The compound 25-amino-1α,3β-dihydroxy-9,10-secocholesta-5(Z),7,10(19)-triene [Formula (I)—A =(A-2), R=H, $R^1$=$R^2$=$CH_3$, $R^3$=α-$CH_3$, $R^4$=$R^5$=H, Y=$(CH_2)_3$] is prepared by similar reaction according to steps (a)–(d) above of the product of Preparation 6(d).

The compound 25-amino-1α,3β-dihydroxy-9,10-secocholesta-5(E),7-diene [Formula (I)—A=(A-5), R=H, $R^1$=$R^2$=$CH_3$, $R^3$=α-$CH_3$, $R^4$=$R^5$=H, Y=$(CH_2)_3$] is prepared by similar reaction according to steps (a)–(d) above of the product of Preparation 8(a).

The compound 25-amino-1α,3β-dihydroxy-9,10-secocholesta-5(Z),7-diene [Formula (I)—A=(A-4), R=H, $R^1$=$R^2$=$CH_3$, $R^3$=α-$CH_3$, $R^4$=$R^5$=H, Y=$(CH_2)_3$] is prepared by similar reaction according to steps (a)–(d) above of the product of Preparation 8(b).

The compound 25-amino-1α,3β-dihydroxy-10-spirocyclopropyl-9,10-secocholesta-5(E),7-diene [Formula (I)—A=(A-7), R=H, $R^1$=$R^2$=$CH_3$, $R^3$=α-CH3, $R^4$=$R^5$=H, Y=$(CH_2)_3$] is prepared by similar reaction according to steps (a)–(d) above of the product of Preparation 8(c).

The compound 25-amino-1α,3β-dihydroxy-10-spirocyclopropyl-9,10-secocholesta-5(Z),7-diene (Formula (I)—A=(A-6), R=H, $R^1$=$R^2$=$CH_3$, $R^3$=α-$CH_3$, $R^4$=$R^5$=H, Y=$(CH_2)_3$] is prepared by similar reaction according to steps (a)–(d) above of the product of Preparation 8(d).

The compound 25-amino-1α,3β-dihydroxy-20-epi-19-nor-9,10-secocholesta-5,7-diene [Formula (I)—A=(A-8), R=H, $R^1$=$R^2$=$CH_3$, $R^3$=β-$CH_3$, $R^4$=$R^5$=H, Y=$(CH_2)_3$] is prepared by similar reaction according to steps (a)–(d) above of the product of Preparation 8(e).

EXAMPLE 5 a) 1α,3β-Bis-triisopropylsilyloxy-24-homo-9,10-secochola-5(E),7,10(19)-triene-24-carbonitrile [Formula (II)—A=(A-3), $R^3$=α-$CH_3$ $R^4$=$R^5$=(i-Pr)$^3$ Si, Y=$(CH_2)_4$]

Acetonitrile (0.32 ml) in tetrahydrofuran (2 ml) was added dropwise at −78° to a solution of butyl lithium (3.75 ml of a 1.6M solution in hexane) and tetrahydrofuran (4 ml). After 50 minutes storage at −78° all but a 0.7 mMole portion of the solution (presumed to contain a total of 6 mMoles) was expelled and the remaining portion was treated with a solution of 1α,3-bis-triisopropylsilyloxy-24-bromo-9,10-secochola-5(E),7,10(19)-triene [Formula (V)—A=(A-3), $R^3$=α-$CH_3$, $R^4$=$R^5$=(i-Pr)$_3$ Si, L=Br, Y=$(CH_2)_3$] (190 mg) in tetrahydrofuran (3.05 ml). After 40 minutes storage at −780° the mixture was allowed to warm to −30°, kept at that temperature for 60 minutes (starting material no longer present by TLC), then cooled to −78°. Thereafter the reaction mixture was treated with aqueous ammonium chloride and the product was extracted into diethyl ether. The crude product was purified by chromatography to give the title compound (156 mg). UV (EtOH) $\lambda_{max}$ 267-8, $\lambda_{min}$ 228 nm; NMR (CCl$_4$) δ 0.53 (s, 18-H's), 4.96, (s, 19-H's), 5.53–6.26 (ABq, 6,7-H's).

b) 25-Amino-1α,3β-bis-triisopropylsilyloxy-24-homo-9,10-secocholesta-5(E),7,10(19)-triene [Formula (I)—A=(A-3), R=H, $R^1$=$R^2$=$CH_3$, $R^3$=α-$CH_3$ $R^4$=$R^5$=(i-Pr)$_3$Si, Y=$(CH_2)_4$]

A solution of cerous chloride (381 mg) in tetrahydrofuran (3 ml) was treated at 0° with sufficient methyl lithium (1.2 mL of a [?] molar solution in hexane) to produce a persistent yellow colour. The solution was cooled to −78°, a further portion of methyl lithium (1.4 ml) was added and the mixture was kept at −78° for 30 minutes to complete formation of the organocerium reagent. The nitrile from (a) above (180 mg in 2.05 ml tetrahydrofuran) was added at −78°, and the reaction mixture was stirred at that temperature for an additional 60 minutes, warmed to −30°, cooled to −78°, and treated with aqueous ammonium hydroxide. The crude product was filtered through Celite (methylene chloride/ diethyl ether) and purified by chromatography to give the title compound (125 mg). UV (Et$_2$O) $\lambda_{max}$ 267-8, $\lambda_{min}$ 227-8 nm; NMR (CCl$_4$) δ 0.53 (s, 18-H's), 4.8, (s, 19-H's), 5.53–6.26 (ABq, 6,7-H's).

c) 25-Amino-1α,3β-bis-triisopropylsilyloxy-24-homo-9,10-secocholesta-5(Z),7,10(19)-triene [Formula (I)—A=(A-2), R=H, $R^1$=$R^2$=$CH_3$,$R^3$=α-$CH_3$ $R^4$=$R^5$=(i-Pr)$_3$ Si, Y=$(CH_2)_4$]

The amine from (b) above (125 mg) was photoisomerised by irradiation for 40 minutes in solution in benzene (18 ml) containing phenazine (61 mg). Chromatography afforded the title compound (88 mg). UV (Et$_2$O) $\lambda_{max}$ 263, $\lambda_{min}$ 226-7 nm; NMR (CDCl$_3$) δ 0.53 (s, 18-H's), 4.73, 5.0 (ea. s, 19-H's), 5.6–6.1 (ABq, 6,7-H's).

d) 25-Amino-1α,3β-dihydroxy-24-homo-9,10-secocholesta-5(Z),7,10(19)-triene [Formula (I)—A=(A-2), R=H, R$^1$=R$^2$=CH$_3$, R$^3$=α-CH$_3$, R$^4$=R$^5$=H, Y=(CH$_2$)$_4$]

The silyl ether (40 mg) from (c) above was desilylated by treatment with tetrabutylammonium fluoride (320 μl) in tetrahydrofuran (320 μl) for three hours at room temperature. Chromatography gave the title compound (8.7 mg). UV (EtOH) $\lambda_{max}$ 263, $\lambda_{min}$ 226-7 nm; IR (CHCl$_3$) $\nu_{max}$ 3200–3300, 3600 cm$^{-1}$ (OH, NH); NMR (CDCl$_3$) δ 0.53 (s, 18-H's), 4.9, 5.2 (ea. s, 19-H's), 5.8–6.33 (ABq, 6,7-H's).

e) 25-Amino-1α,3β-dihydroxy-24,26,27-tris-homo-9,10-secocholesta-5(Z),7,10(19)-triene [Formula (I)—A=(A-2), R=H, R$^1$=R$^2$=CH$_3$CH$_2$, R$^3$=α-CH$_3$, R$^4$=R$^5$=H, Y=(CH$_2$)$_4$]

The title compound is prepared by substituting ethyl lithium for methyl lithium in (b) above and continuing the remainder of the procedure.

f) 25-Amino-1α,3β-dihydroxy-24,26,26,26,27,27,27-heptakis-homo-9,10-secocholesta-5(Z),7,10(19)-triene [Formula (I)—A=(A-2), R=H, R$^1$=R$^2$=CH$_3$(CH$_2$)$_3$, R$^3$=α-CH$_3$, R$^4$=R$^5$=H, Y=(CH$_2$)$_4$]

The title compound is prepared by substituting butyl lithium for methyl lithium in (b) above and continuing the remainder of the procedure.

g) 25-Amino-1α,3β,23-trihydroxy-9,10-secocholesta-5(Z),7,10(19)-triene [Formula (I)—A=(A-2), R=H, R$^1$=R$^2$=CH$_3$, R$^3$=α-CH$_3$, R$^4$=R$^5$=H, Y=CH$_2$CHOHCH$_2$]

The title compound is prepared by substituting 1α,3-bis-triisopropylsilyloxy-23-nor-9,10-secopregna-5(E),7,10(19)-triene-24-carboxaldehyde [Formula (VII)—A=(A-3), R$^3$=α-CH$_3$, R$^4$=R$^5$=(i-Pr)$_3$ Si, Y$^b$=CH$_2$] for the bromoethyl compound in (a) above and containing the remainder of the procedure.

25-Amino-lx,30-bis-triisopropylsilyloxy-24,26,27-tris-homo-9,10-secocholesta-5(E),7,10(19),22,24(24a)-pentaene [formula (I)—A=(A-3), R=H, R$^1$=R$^2$=CH$_3$CH$_2$, R$^3$=α-CH$_3$, R$^4$=R$^5$=(i-Pr)$_3$ Si, Y=CH=CH—CH=CH] is prepared by substituting ethyl lithium for the methyl lithium and 1α,3β-bis-triisopropylsilyloxy-24-cyano-24-homo-9,10-secochola-5(E),7,10(19),22(E),24(E)-pentaene [Formula (II)—A=(A-3), R$^1$=α-CH$_3$, R$^4$=R$^5$(i-Pr)$_3$ Si, Y=CH=CH—CH=CH] (Preparation 9 (b)) for the nitrile in (b) above.

Isomerisation and desilylation afford 25-amino-1α,3β-dihydroxy-24,26,27-tris-homo-9,10-secocholesta-5(Z),7,10(19), 22,24(24a)-pentaene [Formula (I)—A=(A-2), R=H, R$^1$=R$^2$=CH$_3$CH$_2$, R$^3$=α-CH$_3$, R$^4$=R$^5$=OH, Y=CH=CH—CH=CH].

EXAMPLE 6

25-Acetamido-1α,3β-bis-triisopropylsilyloxy-2A-homo-9,10-secocholesta-5(Z),7,10(19)-triene [Formula (I)—A=(A-2), R=CH$_3$CO, R$^1$=R$^2$=CH$_3$, R$^3$=α-CH$_3$, R$^4$=R$^5$=(i-Pr)$_3$ Si, Y=(CH$_2$)$_4$]

The 25-amino compound from Example 5 (c) above (48 mg) was treated with acetic anhydride (0.026 ml) in pyridine (0.26 ml) and methylene chloride (0.8 ml). After 2 hours storage at room temperature the reaction mixture was cooled, treated with aqueous sodium bicarbonate and stirred for 2 hours, following which the product was extracted into ethyl acetate. Chromatography gave title compound (24 mg). UV (Et$_2$O) $\lambda_{max}$ 262-3, $\lambda_{min}$ 225 nm; IR $\nu_{max}$ (CCl$_4$) 3350, 3220 (NH), 1680 cm$^{-1}$ (CONH); NMR (CCl$_4$) δ 0.53 (s, 18-H's), 1.8 (s, OCCH$_3$), 4.1–4.46 (bm, 1,3-H's), 4.73, 5.06, 5.23 (each s, 19-H's, N—H), 5.66–6.36 (ABq, 6,7-H's)

b) 25-Acetamido-1α,3β-dihydroxy-24-homo-9,10-secocholesta-5(Z),7,10(19)-triene [Formula (I)—A=(A-2), R=CH$_3$CO, R$^1$=R$^2$=CH$_3$, R$^3$=α-CH$_3$, R$^4$=R$^5$=H, Y=(CH$_2$)$_4$]

The silyl ether from (a) above (25 mg) was desilylated by treatment with tetrabutylammonium fluoride (0.030 ml) in tetrahydrofuran (0.30 ml) at room temperature for 4.5 hours. Chromatography gave the title compound (22 mg). UV (EtOH) $\lambda_{max}$ 263, $\lambda_{min}$ 225-6 nm; IR $\nu_{max}$ (CHCl$_3$) 3420, 3600 (NH, OH), 1670 cm3$^1$ (CONH); NMR (CDCl$_3$) δ 0.56 (s, 18-H's), 0.86, 0.93 (d, 21-H's), 1.3 (d, CH$_3$), 1.8 (s, OCCH$_3$), 4.03–4.4 (bm, 1,3-H's), 4.9, 5.1, 5.23 (each s, 19-H's, N—H), 5.8–6.36 (ABq, 6,7-H's). 25-Benzamido-1α,3β-bis- trilsocropylsilyloxy-24-homo-9,10-secocholesta-5(Z),7,10(19)-triene [formula (I)—A=-(A-2), R=C$_6$H$_5$CO, R$^1$=R$^2$=CH$_3$, R$^3$=α-CH$_3$, R$^4$=R$^5$=(i-Pr)$_3$ Si, Y=(CH$_2$)$_4$] is prepared by use of benzoyl chloride and minor modification (Schotten-Baumann) of the procedure of (a) above and may be converted by desilylation into 25-benzamido-1et,30-dihydroxy-24-homo-9,10-secocholesta-5(Z),7,10(19)-triene [formula (I)—A=(A-2), R=C$_6$H$_5$CO, R$^1$=R$^2$=CH$_3$, R$^3$=α-CH$_3$, R$^4$=R$^5$=H, Y=(CH$_2$)$_4$].

EXAMPLE 7 a) 25-Amino-1α,3β-bis-triisopropylsilyloxy-26,27-bis-homo-9,10-secocholesta-5(E),7,10(19)-trien-23-yne [Formula (I)—A=(A-3), R=H, R$^1$=R$^2$=CH$_{3,2}$, R$^3$=α-CH$_3$ R$^4$=R$^5$=(i-Pr)$_3$ Si, Y=CH$_2$—C≡C]

A solution of 3-amino-3-ethyl-1-pentyne [Formula (VI) —R=H, R$^1$=R$^2$=CH$_3$CH$_2$, n=O] (1.05 ml) in hexane (10.5 ml) containing hexamethylphosphoramide (0.9 ml) was treated at 0° with butyl lithium (4.5 ml of a 1.4M solution in hexane), then kept with stirring at 5° for 30 minutes, followed by 1.25 hours at room temperature. All but 2.5 mMole of the solution (presumed to contain 6 mMole of acetylide anion) was expelled. The remaining 2.5 mMole of anion was treated with 1α,3β-bis-triisopropylsily-loxy-20α-bromomethyl-9,10-secopregna-5(E),7,10(19)-triene [Formula (V)—A=(A-3), R$^3$=α-CH$_3$ R$^4$=R$^5$=(i-Pr)$_3$ Si, L=Br, Y$^a$=CH$_2$] (200 mg) and the resulting mixture stirred at 35° for 21 hours. The reaction mixture was then cooled, treated with aqueous ammonium chloride, and the product was extracted into ether. Chromatography gave the title compound (68 mg) UV (Et$_2$O) $\lambda_{max}$ 267, $\lambda_{min}$ 226 nm; NMR (CDCl$_4$) δ 0.5 (s, 18-H's), 4.83 (S, 19-H's), 5.6–6.36 (ABq, 6,7-H's).

b) 25-Amino-1α,3β-bis-triisopropylsilyloxy-26,27-bis-homo-9,10-secocholesta-5(Z), 7,10(19)-trien-23-yne [Formula (I)—A=(A-2), R=H, R$^1$=R$^2$=CH$_3$CH$_2$, R$^3$=α-CH$_3$ R$^4$=R$^5$=(i-Pr)$_3$ Si, Y=CH$_2$—C≡C]

The product from (a) above (95 mg) was photoisomerized by irradiation for 30 minutes in solution in benzene (14 ml) containing phenazine (50 mg). Chromatography gave the title compound (66.5 mg). UV (Et$_2$O) $\lambda_{max}$ 260-1, $\lambda_{min}$ 226 nm; NMR (CCl$_4$) δ 0.50 (S, 18-H's), 4.1–4.43 (bm, 1,3-H's), 4.73, 5.03 (each s, 19-H's), 5.9–6.23 (ABq, 6,7-H's).

c) 25-Amino-1α,3β-dihydroxy-26,27-bis-homo-9,10-secocholesta-5(Z),7,10(19)-trien-23-yne [Formula (I)—A= (A-2), R=H R$^1$=R$^2$=CH$_3$CH$_2$, R$^3$=α-CH$_3$ R$^4$=R$^5$=H, Y=CH$_3$—C≡C]

The silyl ether from (b) above (67 mg) was desilylated by treatment with tetrabutylammonium fluoride (0.5 ml of a 1M solution in tetrahydrofuran) in tetrahydrofuran (0.5 ml) at room temperature overnight. The product was extracted into chloroform, washed with water and isolated by chromatography to give the title compound (29 mg). UV (EtOH) $\lambda_{max}$ 262-3, $\lambda_{min}$ 225 nm; IR (CHCl$_3$) $\nu_{max}$ 3200–3500, 3600 cm.$^{-1}$ (OH, NH); NMR (CDCl$_3$) δ 0.53 (s, 18-H's), 0.86–1.23 (m, 21-H's and Me-H's of Et's), 1.9 (m, N—H's, exchanges with $D_2O$), 1.36–1.56 (m, Et-H's), 4.03–4.4 (bm, 1,3-H's), 4.86, 5.2 (ea. s, 19-H's), 5.76–6.33 (ABq, 6,7-H's).

By substituting 1α,3β-bis-triisopropylsilyloxy-20β-bromoethyl-9,10-secopregna-5(E),7,10(19)-triene [Formula (V)—A=(A-3), $R^3$=β-$CH_3$, $R^4$=$R^5$=(i-Pr)$_3$ Si, L=Br, Y=($CH_2$)$_2$] for the steroid starting material in (a) above and following the remainder of the procedure one may prepare 25-amino-1α,3β-dihydroxy-20-epi-24,26,27-tris-homo-9,10-secocholesta-5(Z),7,10(19)-trien-24(24a)-yne [Formula (I)—A=(A-2), R=H, $R^1$=$R^2$=$CH_3CH_2$, $R^3$=β-$CH_3$, $R^4$=$R^5$=H, Y=($CH_2$)$_2$—C≡C—].

By substituting 2-amino-2-methyl-4-pentyne [Formula (VI)—R=H, $R^1$=$R^2$=$CH_3$, n=1] for the alkyne in (a) above and following the remaining procedures one obtains 25-amino-1α,3β-dihydroxy-24-homo-9,10-secocholesta-5 (Z),7,10(19)-trien-24(24a)-yne [Formula (1) A=(A-2), R=H, $R^1$=$R^2$=$CH_3$,$R^3$=α-$CH_3$, $R^4$=$R^5$=H, Y=$CH_2$—C≡C—$CH_2$].

EXAMPLE 8
Conversion of alkynylenyl side-chain to alkylenyl

The triene system of any of the steroid alkynes prepared acording to Example 7, preferably having 5(E) configuration, is protected from hydrogenation by reaction with a diazo dienophile (preferably phthalazine dione) to form a Diels Alder adduct (between the 6- and 19-positions). (GB-A-2114570). The resulting adduct (about 100 mg) in a mixture of ethanol (5 ml) and benzene (5 ml) containing fresh platinum on charcoal (5%, 100 mg) and sodium bicarbonate (50 mg) is kept under an atmosphere of hydrogen until 2 molecular equivalents of hydrogen have been consumed (about 20 hours). Filtration through Celite and removal of the solvents gives substantially pure product. The phthalizine group is then removed as described in the aforementioned British patent and the resulting 5(E) vitamin may be photoisomerised and the silyl groups removed as in Example 7. In this fashion one may obtain 25-amino-1α,3β-dihydroxy-20-epi-24,26,27-tris-homo-9,10-secocholesta-5(Z),7,10(19)-triene [Formula (I) A=(A-2),R=H, $R^1$=$R^2$=$CH_3CH_2$, $R^3$=β-$CH_3$, $R^4$=$R^5$-=H, Y=($CH_2$)$_4$] from product of Example 7 (a).

EXAMPLE 9
a) 25-Amino-1α,3β-bis-triisopropylsilyloxy-22-hydroxy-26,27-bis-homo-9,10-secocholesta-5(E),7,10(19)-trien-23-yne [Formula (I)—A=(A-3), R=H, $R^1$=$R^2$=$CH_3CH_2$, $R^3$=α$CH_3$, $R^4$=$R^5$=(i-Pr)$_3$ Si, Y=CHOH—C≡C]

A solution of 3-amino-3-ethyl-1-pentyne [Formula (VI) —R=H, $R^1$=$R^2$=$CH_3CH_2$, n=0] (0.78 ml) in hexane (6.5 ml) containing hexamethylphosphoramide (0.6 ml) was treated at 5° with butyl lithium (3 ml of a 1.4M solution in hexane), then kept with stirring at 5° for 30 minutes, followed by 1.25 hours at room temperature. A portion of the solution (⅕, presumed to contain about 0.75 mMole of acetylide anion) was added at −78° to a solution of 1α,3β-bis-triisopropylsilyloxy-20α-formyl-9,10-secopregna-5(E),7,10 (19)-triene [Formula (VII)—A=(A-3), $R^3$=α-$CH_3$, $R^4$=$R^5$=(i-Pr)$_3$ Si, $Y^b$=valence bond] (100 mg) and the resulting mixture stirred while the temperature was allowed slowly to rise to 200 (by which time the aldehyde had been consumed). The reaction mixture was then cooled to −78°, treated with aqueous ammonium chloride, and the product was extracted into ether. Chromatography gave the title compound (94 mg). TV (Et$_2$O) $\lambda_{max}$ 268-9, $\lambda_{min}$ 227 nm; NMR (CCl$_4$) δ 0.55 (s, 18-H's), 4.23–4.56 (bm, 1,3-H's), 4.83 (s, 19-H's), 5.6–6.33 (ABq, 6,7-H's).

b) 25-Amino-1α,3β-bis-triisopropylsilyloxy-22-hydroxy-26,27-bis-homo-9,10-secocholesta-5(Z),7,10(19)-trien-23-yne [Formula (I)—A=(A-2), R=H, $R^1$=$R^2$=$CH_3CH_2$, $R^3$=α-$CH_3$, $R^4$=$R^5$=(i-Pr)$_3$ Si, Y=CHOH—C≡C]

The product from (a) above (94 mg) was photoisomerized by irradiation for 40 minutes in solution in benzene (11 ml) containing phenazine (40 mg). Chromatography gave the title compound (68 mg). UV (Et$_2$O) $\lambda_{max}$ 261-2, $\lambda_{min}$ 225 nm; NMR (CCl$_4$) δ 0.53 (s, 18-H's), 4.16–4.5 (bm, 1,3-H's), 4.73, 5.1 (each s, 19-H's), 5.73–6.06 (ABq, 6,7-H's).

c) 25-Amino-1α,3β,22-trihydroxy-26,27-bis-homo-9,10-secocholesta-5(Z),7,10(19)-trien-23-yne [Formula (I)—A=(A-2), R=H, $R^1$=$R^2$=$CH_3CH_2$, $R^3$=α-$CH_3$, $R^4$=$R^5$=H, Y=CHOH—C≡C]

The silyl ether from (b) above (68 mg) was desilylated by treatment with tetrabutylammonium fluoride (0.5 ml of a 1M solution in tetrahydrofuran) in tetrahydrofuran (0.5 ml) at room temperature for 16 hours. TLC showed some starting material so a further portion of tetrabutylammonium fluoride (0.4 ml) was added and the reaction allowed to continue for a further 2 hours. The product was extracted into chloroform, washed with water and isolated by chromatography (2×) followed by partition between methylene chloride and water to give the title compound (18 mg). UV (EtOH) $\lambda_{max}$ 263-4, $\lambda_{min}$ 225-6 nm; IR (CDCl$_3$) $v_{max}$ 3250–3450, 3600 cm$^{-1}$ (OH, NH); NMR (CDCl$_3$) δ 0.53 (s, 18-H's), 0.83–1.23 (m, 21-H's and Me-H's of Et's), 1.83 (m, N—H's?), 1.36–1.56 (m, Et-H's), 4.1–4.5 (bm, 1,3-H's), 4.9, 5.23 (ea. s, 19-H's), 5.83–6.36 (ABq, 6,7-H's).

By substituting 1α,3β-bis-triisopropylsilyloxy-23-nor-9,10-secopregna-5(E),7,10(19)-triene-24-carboxaldehyde [Formula (VII)—A=(A-3), $R^3$=α-$CH_3$, $R^4$=$R^5$=(i-Pr)$_3$ Si, $Y^b$=$CH_2$] in (a) above and following the subsequent procedure one may prepare 25-amino-1a,3p,23-trihydroxy-24,26,27-tris-homo-9,10-secocholesta-5(Z),7,10(19)-triene-24 (24a)-yne [Formula (I)—A=(A-2), R=H, $R^1$=$R^2$=$CH_3CH_2$, $R^3$=α-$CH_3$, $R^4$=$R^5$=H, Y=$CH_2$CHOH—C≡C].

By substituting 1,1-dimethylpropargyl amine [Formula (VI)—R=H, $R^1$=$R^2$=$CH_3$, n=0] for the aminoalkyne in (a) above and following the subsequent procedures one may prepare 25-amino-1α,3β,22-trihydroxy-9,10-secocholesta-5 (Z),7,10(19)-trien-23-yne [Formula (I)—A=(A-2), R=H, $R^1$=$R^2$=$CH_3$, $R^3$=α-$CH_3$, $R^4$=$R^5$=H, Y=CHOH—C≡C].

d) 25-Amino-1α,3β-dihydroxy-22-methoxy-26,27-bis-homo-9,10-secocholesta-5(Z),7,10(19)-trien-23-yne [Formula (I)—A=(A-2), R=H, $R^1$=$R^2$=$CH_3CH_2$, $R^3$=α-$CH_3$ $R^4$=$R^5$=H, Y=CH(OCH$_3$)—C≡C]

The title compound is prepared by methylation of 25-amino-1α,3β-bis-triisopropylsilyloxy-22-hydroxy-26,27-bis-homo-9,10-secocholesta-5(Z),7,10(19)-trien-23-yne [Formula (I)—A=(A-2), R=H, $R^1$=$R^2$=$CH_3CH_2$, $R^3$=α-$CH_3$, $R^4$=$R^5$=(i-Pr)$_3$ Si, Y=CHOH—C≡C] from (b) above using a substantial excess of potassium t-butoxide in benzene containing 18-crown-6, followed by careful addition of methyl iodide (TLC control) and then removing the silyl groups as in (c) above.

25-Amino-1α,3β-dihydroxy-22-ethoxy-26,27-bis-homo-9,10-secocholesta-5(Z),7,10(19)-trien-23-yne [Formula (I)—A=(A-2), R=H, $R^1$=$R^2$=$CH_3CH_2$, $R^3$=α-$CH_3$ $R^4$=$R^5$=H, Y=CH(OCH$_2$CH$_3$)—C≡C] and 25-amino-1α,3β-dihydroxy-22-propoxy-26,27-bis-homo-9,10-secocholesta-5(Z),7,10(19)-trien-23-yne (Formula (I)—A=(A-2), R=H, $R^1$=$R^2$=$CH_3CH_2$, $R^3$=α-$CH_3$ $R^4$=$R^5$=H, Y=CH (OCH$_2$CH$_2$CH$_3$)—C≡C] are prepared as in (d) above by replacement of methyl iodide by ethyl or propyl iodides respectively.

EXAMPLE 10
a) N-ethyl-25-amino-1α,3β-bis-triisopropylsilyloxy-24-homo-9,10-secocholesta-5(Z),7,10(19)-triene [Formula (I)

—A=(A-2), R=CH$_3$CH$_2$, R$^1$=R$^2$=CH$_3$, R$^3$=α-CH$_3$, R$^4$=R$^5$= (i-pr)$_3$ Si, L=Br, Y=CCH$_2$)$_4$]

A solution of 25-acetamido-l1,3β-bis-triisopropylsilyloxy- 24-homo-9,10-secocholesta-5(Z), 7,10(19)-triene [Formula (I)—A=(A-2), R=CH$_3$CO, R$^1$=R$^2$=CH$_3$, R$^3$=α-CH$_3$, R$^4$=R$^5$=(i-Pr)$_3$ Si, Y=(CH$_2$)$_4$] prepared as in Example 6 (a) (44 mg) in tetrahydrofuran (1.5 ml) containing lithium aluminium hydride (35 mg) is heated under reflux with stirring until the starting material is consumed (about 2.5 hours by TLC analysis), then cooled and treated with a few drops of water. The reaction mixture is treated with sodium sulphate, diluted with ether, and the etheral layer is decanted. Evaporation of the solvent affords the title compound.

b) N-ethyl-25-amino-1α,3β-dihydroxy-24-homo-9,10-secocholesta-5(Z),7,10(19)-triene [Formula (I)—A=(A-2), R=CH$_3$CH$_2$, R$^1$=R$^2$=CH$_3$, R$^3$=α-CH$_3$, R$^4$=R$^5$=H, Y=(CH$_2$)$_4$]

The title compound is obtained by desilylation of the product of (a) above in similar manner to Example 1 (d).

N-propyl-25-amino-1α,3β-dihydroxy-24-homo-9,10-secocholesta-5(Z),7,10(19)-triene [Formula (I)—A=(A-2), R=CH$_3$CH$_2$CH$_2$, R$^1$=R$^2$=CH$_3$, R$^3$=α-CH$_3$, R$^4$=R$^5$=H, Y=(CH$_2$)$_4$] is similarly prepared by substituting 25-propionamido-1α,3β-bis-triisopropylsilyloxy-24-homo-9,10-secocholesta-5(Z),7,10(19)-triene [Formula (I)—A=(A-2), R=CH$_3$CH$_2$CO, R$^1$=R$^2$=CH$_3$, R$^3$=α-CH$_3$, R$^4$=R$^5$=(i-Pr)$_3$ Si, Y=(CH$_2$)$_4$] (prepared by substituting propionyl chloride in Example 6 and increasing the reaction time to 4 hours) in (a) above and following the remainder of the procedure.

We claim:

1. A compound of general formula (I)

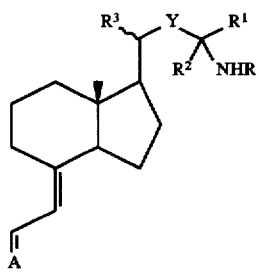

where

R represents a hydrogen atom, an aliphatic, cycloaliphatic or araliphatic group, or an acyl group comprising an aliphatic, cycloaliphatic, arylaliphatic or aryl group linked to the nitrogen atom by way of a carbonyl group;

R$^1$ and R$^2$ are each selected from lower alkyl and cycloalkyl groups or together with the carbon atom to which they are attached form a lower cycloalkyl group;

R$^3$ represents a methyl group having α- or β-configuration;

Y represents a lower alkylene, alkenylene or alkynylene group optionally substituted by a hydroxyl, etherified hydroxyl or esterified hydroxyl group; and A= represents a cyclohexylidene moiety characteristic of the A-ring of a 1α-hydroxylated vitamin D or analogue thereof.

2. A compound as claimed in claim 1 wherein R represents a hydrogen atom, a lower alkyl or a lower alkanoyl group.

3. A compound as claimed in claim 1 in which R$^1$ and R$^2$ are each selected from methyl, ethyl, propyl and butyl groups.

4. A compound as claimed in claim 1 wherein Y is a straight chain group containing 3–6 carbon atoms.

5. A compound as claimed in claim 4 wherein Y is selected from trimethylene, tetramethylene, pentamethylene, hexamethylene, buta-1,3-dienylene, propynylene, but-1-ynylene and but-2-ynylene.

6. A compound as claimed in claim 1 wherein Y carries a hydroxy, etherified hydroxy or esterified hydroxy group in a position α-, β- or γ- to the group —C(R$^1$) (R$^2$).NHR or α- to any triple bond present in the group Y.

7. A compound as claimed in claim 1 wherein A= represents one of the groups

and

where R$^4$ and R$^5$ are each selected from hydrogen atoms and O-protecting groups.

8. A compound as claimed in claim 7 wherein R$^4$ and R$^5$ represent etherifying silyl groups.

9. A compound as claimed in claim 7 wherein R$^4$ and R$^5$ are selected from hydrogen atoms and metabolically labile etherifying or esterifying groups.

10. A compound as claimed in claim 1 wherein A= represents one of the groups

and

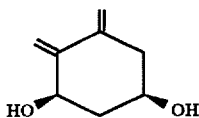
(A-3a)

11. A 20,20-dimethyl, 20-methylene or 20-spirocyclopropyl analogue of a compound as claimed in claim 1.

12. A Pharmaceutical composition comprising an active compound as claimed in claim 1 in admixture with one or more physiologically acceptable carriers or excipients.

13. A method of treatment of a human or animal subject to promote treatment and/or prevention of rickets, osteomalacia, osteoporosis, hypoparathyroidism, hypophosphataemia, hypocalcaenia and/or associated bone disease, hypocalcaemic tetiary, renal failure, renal osteodystraphy, biliary cirrhosis, steatorrhea, secondary hypocalcaemia and/or associated bone disease, wound healing, fertility control, suppression of parathyroid hormone or management of disorders involving blood clotting or to combat neoplastic disease, infection, bone disease, autoimmune disease, host-graft reaction, transplant rejection, inflammatory disease, neoplasia, hyperplasia, myopathy, enteropathy, spondylitic heart disease, dermatological disease, hypertension, rheumatoid arthritis, psoriatic arthritis, secondary hyperparathyroidism, asthma, cognitive impairment or senile dementia, comprising administration to said subject of an effective amount of an active compound as claimed in claim 1.

14. A process for the preparation of a compound of general formula (I) as defined in claim 1 which comprises one or more of:

A) isomerising a 5,6-trans isomer of general formula (I) to a corresponding 5,6-cis isomer, followed if necessary and/or desired by removal of any O-protecting groups;

B) hydroxylating a 1-unsubstituted-5,6-trans analogue of a compound of general formula (I) to prepare a 5,6-trans isomer of general formula (I), followed if necessary and/or desired by isomerisation and/or removal of any O-protecting group;

C) reacting a compound containing a precursor for the desired 17-position side chain in one or more stages and with one or more reactants serving to form the desired side chain, followed if necessary and/or desired by isomerisation and/or removal of any O-protecting groups; or D) reacting a compound of formula (I) to modify the substitution pattern about the A= group, followed if necessary and/or desired by isomerisation and/or removal of protecting groups.

15. A compound:

25-amino-1α,3β-dihydroxy-9,10-secocholesta-5(Z),7,10(19)-triene;

25-amino-1α,3β-dihydroxy-23,24-bisnor-9,10-secocholesta-5(Z),7,10(19)-triene;

25-acetamido-1α,3β-dihydroxy-9,10-secocholesta-5(Z),7,10(19)-triene;

25-amino-1α,3β-dihydroxy-20-epi-9,10-secocholesta-5(Z),7,10(19)-triene;

25-amino-1α,3β-dihydroxy-24-homo-9,10-secocholesta-5(Z),7,10(19)-triene;

25-amino-1α,3β-dihydroxy-9,10-secocholesta-5(Z),7,10(19)-triene;

25-amino-1α,3β-dihydroxy-9,10-secocholesta-5(E),7,diene;

25-amino-1α,3β-dihydroxy-9,10-secocholesta-5(Z),7,diene;

25-amino-1α,3β-dihydroxy-10-spirocyclopropyl-9,10-secocholesta-5(Z),7,10(19)-triene;

25-amino-1α,3β-dihydroxy-10-spirocyclopropyl-9,10-secocholesta-5(E),7,10(19)-triene;

25-amino-1α,3β-dihydroxy-20-epi-19-nor-9,10-secocholesta-5,7-diene;

25-amino-1α,3β-dihydroxy-24,26,27-tris-homo-9,10-secocholesta-5(Z),7,10(19)-triene;

25-amino-1α,3β-dihydroxy-24,26,26,26,27,27,27-heptakis-homo-9,10-secocholesta-5(Z),7,10(19)-triene;

25-acetamido-1α,3β-dihydroxy-24-homo-9,10-secocholesta-5(Z),7,10(19)-triene;

25-amino-1α,3β-dihydroxy-26,27-bis-homo-9,10-secocholesta-5(Z),7,10(19)-trien-23-yne;

25-amino-1α,3β-dihydroxy-20-epi-24,26,27-tris-homo-9,10-secocholesta-5(Z),7,10(19)-trien-24(24a)-yne;

25-amino-1α,3β-dihydroxy-24-homo-9,10-secocholesta-5(Z),7,10(19)-trien-24(24a)-yne;

25-amino-1α,3β-dihydroxy-20-epi-24,26,27-tris-homo-9,10-secocholesta-5(Z),7,10(19)-triene;

25-amino-1α,3β-trihydroxy-26,27-bis-homo-9,10-secocholesta-5(Z),7,10(19)-trien-23-yne;

25-amino-1α,3β,23-trihydroxy-24,26,27-tris-homo-9,10-secocholesta-5(Z),7,10(19)-trien-24(24a)-yne;

25-amino-1α,3β,22-trihydroxy-9,10-secocholesta-5(Z),7,10(19)-trien-23-yne;

25-amino-1α,3β-dihydroxy-22-methoxy-9,10-secocholesta-5(Z),7,10(19)-trien-23-yne;

25-amino-1α,3β-dihydroxy-22-ethoxy-9,10-secocholesta-5(Z),7,10(19)-trien-23-yne;

25-amino-1α,3-dihydroxy-22-propoxy-9,10-secocholesta-5(Z),7,10(19)-trien-23-yne;

N-ethyl-25-amino-1α,3β-dihydroxy-24-homo-9,10-secocholesta-5(Z),7,10(19)-triene;

25-benzamido-1α,3β-dihydroxy-24-homo-9,10-secocholesta-5(Z),7,10(19)-triene; or 25-amino-1α,3β-dihydroxy-24,26,27-tris-homo-9,10-secocholesta-5(Z),7,10(19),22,24(24a)-pentaene.

* * * * *